United States Patent
Ohtomo et al.

(10) Patent No.: US 10,451,627 B2
(45) Date of Patent: Oct. 22, 2019

(54) METHOD FOR ASSAYING SOLUBLE GPC3 PROTEIN

(71) Applicants: CHUGAI SEIYAKU KABUSHIKI KAISHA, Tokyo (JP); JSR CORPORATION, Tokyo (JP); JSR LIFE SCIENCES CORPORATION, Tokyo (JP)

(72) Inventors: Toshihiko Ohtomo, Tokyo (JP); Jun Amano, Shizuoka (JP); Hideki Adachi, Shizuoka (JP); Tsukasa Suzuki, Shizuoka (JP); Motoaki Mizuuchi, Tokyo (JP); Tetsuji Yamaguchi, Tokyo (JP); Seiki Wakui, Tokyo (JP)

(73) Assignees: CHUGAI SEIYAKU KABUSHIKI KAISHA, Tokyo (JP); JSR CORPORATION, Tokyo (JP); JSR LIFE SCIENCES CORPORATION, Tokyo (JP)

( * ) Notice: Subject to any disclaimer, the term of this patent is extended or adjusted under 35 U.S.C. 154(b) by 0 days.

(21) Appl. No.: 15/107,316

(22) PCT Filed: Jun. 25, 2014

(86) PCT No.: PCT/JP2014/003409
§ 371 (c)(1),
(2) Date: Jun. 22, 2016

(87) PCT Pub. No.: WO2015/097928
PCT Pub. Date: Jul. 2, 2015

(65) Prior Publication Data
US 2017/0010270 A1    Jan. 12, 2017

(30) Foreign Application Priority Data
Dec. 24, 2013 (WO) .................. PCT/JP2013/007529

(51) Int. Cl.
| G01N 33/53 | (2006.01) |
| G01N 33/574 | (2006.01) |
| C07K 16/30 | (2006.01) |
| C07K 16/28 | (2006.01) |
| A61K 39/00 | (2006.01) |

(52) U.S. Cl.
CPC ....... *G01N 33/57438* (2013.01); *C07K 16/28* (2013.01); *C07K 16/303* (2013.01); *A61K 2039/505* (2013.01); *A61K 2039/54* (2013.01); *A61K 2039/545* (2013.01); *C07K 2317/34* (2013.01); *C07K 2317/73* (2013.01); *G01N 2333/4722* (2013.01); *G01N 2400/00* (2013.01); *G01N 2800/52* (2013.01)

(58) Field of Classification Search
CPC ......... G01N 33/57438; G01N 2800/52; G01N 2333/4722; G01N 2400/00; C07K 16/28; C07K 16/303; C07K 2317/34; C07K 2317/73; A61K 2039/545; A61K 2039/54; A61K 2039/505
See application file for complete search history.

(56) References Cited

U.S. PATENT DOCUMENTS

| 5,322,678 A | 6/1994 | Morgan, Jr. et al. |
| 6,436,411 B1 | 8/2002 | Riordan et al. |
| 6,617,156 B1 | 9/2003 | Doucette-Stamm et al. |
| 6,737,056 B1 | 5/2004 | Presta |
| 7,297,775 B2 | 11/2007 | Idusogie et al. |
| 7,317,091 B2 | 1/2008 | Lazar et al. |
| 7,691,586 B2 | 4/2010 | Watanabe et al. |
| 7,744,880 B2 | 6/2010 | Aburatani et al. |
| 7,867,734 B2 | 1/2011 | Nakano et al. |
| 7,871,613 B2 | 1/2011 | Kinoshita et al. |
| 7,919,086 B2 | 4/2011 | Nakano et al. |
| 8,263,077 B2 | 9/2012 | Aburatani et al. |
| 8,497,355 B2 | 7/2013 | Igawa et al. |
| 8,663,929 B2 | 3/2014 | Kataoka et al. |
| 8,937,158 B2 | 1/2015 | Lazar et al. |
| 9,096,651 B2 | 8/2015 | Igawa et al. |
| 9,102,739 B2 | 8/2015 | Lazar et al. |
| 9,513,292 B2 | 12/2016 | Aburatani et al. |
| 2002/0102254 A1 | 8/2002 | Leung et al. |
| 2004/0110226 A1 | 6/2004 | Lazar et al. |
| 2004/0236080 A1 | 11/2004 | Aburatani et al. |
| 2005/0054832 A1 | 3/2005 | Lazar et al. |
| 2005/0233392 A1 | 10/2005 | Filmus et al. |
| 2006/0014223 A1 | 1/2006 | Aburatani et al. |
| 2006/0040325 A1 | 2/2006 | Wu et al. |
| 2006/0167232 A1 | 7/2006 | Aburatani et al. |
| 2006/0188510 A1 | 8/2006 | Aburatani et al. |

(Continued)

FOREIGN PATENT DOCUMENTS

| CA | 2451493 A1 | 1/2003 |
| CA | 2801911 A1 | 3/2004 |

(Continued)

OTHER PUBLICATIONS

Brown et al J. Immuno. May 1996, 3285-91.*
Vajdos et al. (J. Mol. Biol. 2002, Jul. 5, 320(2):415-28 at 416).*
Rudikoff et al. (PNAS USA (1982) 79:1979-1983.*
Van Regenmortel, A Companion to Methods of Enzymology 9:465-472, 1996.*
Kim et al (PNAS 9, 2011;vol. 108, No. 32, p. 13122-13117.*
Lei, Jun-hua; et al (2013. Abstract;Jiefangjun Yiyao Zazhi, vol. 25, Issue: 8, pp. 26-28, Journal, 2013).*
Zhang (Journal of Pharmaceutical Analysis 2012;2(2):130-135).*

(Continued)

*Primary Examiner* — Julie Wu
*Assistant Examiner* — Carmencita M Belei
(74) *Attorney, Agent, or Firm* — Sughrue Mion, PLLC

(57) ABSTRACT

The present invention relates to a method for assaying soluble GPC3 protein in a test sample, comprising using two different antibodies binding to different epitopes present in the N-terminal region of GPC3 protein.

6 Claims, 5 Drawing Sheets
Specification includes a Sequence Listing.

(56) References Cited

U.S. PATENT DOCUMENTS

| | | |
|---|---|---|
| 2006/0246550 A1 | 11/2006 | Okumura |
| 2007/0190599 A1 | 8/2007 | Nakano et al. |
| 2007/0269444 A1 | 11/2007 | Kinoshita et al. |
| 2008/0003623 A1 | 1/2008 | Nakajima et al. |
| 2008/0008710 A1 | 1/2008 | Aburatani et al. |
| 2008/0124330 A1 | 5/2008 | Nakano et al. |
| 2008/0138827 A1 | 6/2008 | Watanabe et al. |
| 2008/0166756 A1 | 7/2008 | Tsuchiya et al. |
| 2009/0060907 A1 | 3/2009 | Aburatani et al. |
| 2010/0167315 A1 | 7/2010 | Thibault et al. |
| 2010/0239577 A1 | 9/2010 | Igawa et al. |
| 2010/0248359 A1 | 9/2010 | Nakano et al. |
| 2011/0033452 A1 | 2/2011 | Nakano et al. |
| 2011/0091907 A1 | 4/2011 | Kataoka et al. |
| 2011/0104157 A1 | 5/2011 | Kinoshita et al. |
| 2015/0098941 A1 | 4/2015 | Lazar et al. |
| 2015/0210763 A1 | 7/2015 | Kuramochi et al. |
| 2015/0259417 A1 | 9/2015 | Nakano et al. |
| 2015/0285806 A1 | 10/2015 | Ohtomo et al. |
| 2015/0315278 A1 | 11/2015 | Igawa et al. |

FOREIGN PATENT DOCUMENTS

| | | |
|---|---|---|
| CN | 1678740 A | 10/2005 |
| CN | 101377506 A | 3/2009 |
| CN | 102027372 A | 4/2011 |
| CN | 102046200 A | 5/2011 |
| CN | 102276721 A | 12/2011 |
| EP | 0329185 A2 | 8/1989 |
| EP | 1411118 A1 | 4/2004 |
| EP | 1 541 686 A1 | 6/2005 |
| EP | 1 548 442 A1 | 6/2005 |
| EP | 1541680 A1 | 6/2005 |
| EP | 1674111 A1 | 6/2006 |
| EP | 1816140 A1 | 8/2007 |
| EP | 1829962 A1 | 9/2007 |
| EP | 1548442 B1 | 1/2011 |
| EP | 2647706 A1 | 10/2013 |
| EP | 2863224 A1 | 4/2015 |
| EP | 2 937 697 A1 | 10/2015 |
| JP | H02-28200 A | 1/1990 |
| JP | 2007-93274 A | 4/2007 |
| JP | 2007-300927 A | 11/2007 |
| JP | 2009-232848 A | 10/2009 |
| JP | 2011-68682 A | 4/2011 |
| JP | 2015511702 A | 4/2015 |
| RU | 2001124907 A | 6/2003 |
| WO | 00/47228 A1 | 8/2000 |
| WO | 02/40545 A2 | 5/2002 |
| WO | 03/000883 A1 | 1/2003 |
| WO | 03/100449 A2 | 12/2003 |
| WO | 2004/022739 A1 | 3/2004 |
| WO | 2004/023145 A1 | 3/2004 |
| WO | 2004022597 A1 | 3/2004 |
| WO | 2004022754 A1 | 3/2004 |
| WO | 2004/029207 A2 | 4/2004 |
| WO | 2004/038420 A1 | 5/2004 |
| WO | 2004/099249 A2 | 11/2004 |
| WO | 2005023301 A1 | 3/2005 |
| WO | 2005/106485 A1 | 11/2005 |
| WO | 2006/006693 A1 | 1/2006 |
| WO | 2006/038588 A1 | 4/2006 |
| WO | 2006/046751 A1 | 5/2006 |
| WO | 2006/067913 A1 | 6/2006 |
| WO | 2007/005612 A2 | 1/2007 |
| WO | 2007/047291 A2 | 4/2007 |
| WO | 2007/059782 A1 | 5/2007 |
| WO | 2007/081790 A2 | 7/2007 |
| WO | 2007137170 A2 | 11/2007 |
| WO | 2008/032217 A2 | 3/2008 |
| WO | 2009/041062 A1 | 4/2009 |
| WO | 2009/116659 A1 | 9/2009 |
| WO | 2009/122667 A1 | 10/2009 |
| WO | 2012/145469 A1 | 10/2012 |
| WO | 2013/070468 A1 | 5/2013 |
| WO | 2013118858 A1 | 8/2013 |
| WO | 2013127465 A1 | 9/2013 |
| WO | 2013181543 A1 | 12/2013 |
| WO | 2014/097648 A1 | 6/2014 |

OTHER PUBLICATIONS

Creative diagnostics 2009; retrieved from https://www.cd-bioparticles.com/t/Test-Assay-Development_47.html#CLIA).*

Communication dated Jun. 8, 2016 from U.S. Patent & Trademark Office in counterpart U.S. Appl. No. 10/526,741.

Lund et al., "Multiple Interactions of IgG with Its Core Oligosaccharide Can Modulate Recognition by Complement and Huma Fcy Receptor I and Influence the Synthesis of Its Oligosaccharide Chains", The Journal of Immunology, The American Association of Immunologists, 1996, vol. 157, p. 4963-4969.

Lazar, "Declaration of Dr. Greg A. Lazar Under 35 U.S.C. §1.131" dated Dec. 27, 2010 submitted in U.S. Patent Appl. No. 11/841,654, p. 1-4 (total 141 pages).

Communication dated Mar. 3, 2017 from the Indian Patent Office in Indian Application No. 2347/CHENP/2008.

Communication dated Mar. 24, 2017 from U.S. Patent & Trademark Office in U.S. Appl. No. 14/629,967.

Communication dated Apr. 4, 2017 from U.S. Patent & Trademark Office in U.S. Appl. No. 14/505,932.

Llovet et al., "Hepatocellular carcinoma," The Lancet, Dec. 6, 2003; vol. 362: pp. 1907-1917.

Bosch et al., "Primary Liver Cancer: Worldwide Incidence and Trends," Gastroenterology, 2004; 127: S5-S16.

Takenaka et al., "Results of 280 Liver Resections for Hepatocellular Carcinoma," Arch Surg/vol. 131, Jan. 1996; pp. 71-76.

Yeo et al., "Randomized Phase III Study of Doxorubicin Versus Cisplatin/Interferon alpha-2b/Doxorubicin/Fluorouracil (PIAF) Combination Chemotherapy for Unresectable Hepatocellular Carcinoma," Journal of the National Cancer Institute, vol. 97, No. 20, Oct. 19, 2005; pp. 1532-1538.

Llovet et al., "Sorafenib in Advanced Hepatocellular Carcinoma," The New England Journal of Medicine 359:4, Jul. 24, 2008; pp. 378-390.

Cheng et al., "Efficacy and safety of sorafenib in patients in the Asia-Pacific region with advanced hepatocellular carcinoma: a phase III randomised, double-blind, placebo-controlled trial," The Lancet, vol. 10, Jan. 2009, pp. 25-34.

De Cat et al., "Processing by proprotein convertases is required for glypican-3 modulation of cell survival, Wnt signaling, and gastrulation movements," The Journal of Cell Biology, vol. 163, No. 3, Nov. 10, 2003; pp. 625-635.

Traister et al., "Mammalian Notum induces the release of glypicans and other GPI-anchored proteins from the cell surface," Biochemical Journal, 2008, pp. 503-511.

Ho et al., "Glypican-3: A new target for cancer immunotherapy," European Journal of Cancer 47 (2011) pp. 333-338.

Zhu et al., "First-in-Man Phase I Study of GC33, a Novel Recombinant Humanized Antibody Against Glypican-3, in Patients with Advanced Hepatocellular Carcinoma," Clinical Cancer Research, 19(4), pp. 920-928, published online Jan. 29, 2013.

Sawada et al., "Phase I Trial of Glypican-3-Derived Peptide Vaccine for Advanced Hepatocellular Carcinoma: Immunologic Evidence and Potential for Improving Overall Survival," Clinical Cancer Research, 18(13); pp. 3686-3696, published online May 10, 2012.

Yamane-Ohnuki et al., "Establishment of FUT8 Knockout Chinese Hamster Ovary Cells: An Ideal Host Cell Line for Producing Completely Defucosylated Antibodies With Enhanced Antibody-Dependent Cellular Cytotoxicity,"Biotechnology and Bioengineering, vol. 87, No. 5, Sep. 5, 2004, pp. 614-622.

Raju et al., "Glycosylation Variations with Expression Systems and Their Impact on Biological Activity of Therapeutic Immunoglobulins," BioProcess International, Apr. 2003, pp. 44-53.

Konno et al., "Fucose content of monoclonal antibodies can be controlled by culture medium osmolality for high antibody-dependent cellular cytotoxicity," Cytotechnology (2012) 64: pp. 249-265.

(56) References Cited

OTHER PUBLICATIONS

Kunkel et al., "Comparisons of the Glycosylation of a Monoclonal Antibody Produced under Nominally Identical Cell Culture Conditions in Two Different Bioreactors," Biotechnology Progress, 2000, vol. 16, pp. 462-470.
International Search Report dated Sep. 30, 2014 from the International Bureau in counterpart International Application No. PCT/JP2014/003409.
Yue Huang et al., "A Sensitive method for protein assays using a peptide-based nano-label: human glypican-3 detection for hepatocellular carcinomas diagnosis", Analyst, 2014, vol. 139, pp. 3744-3747.
Hyun Jung Lee et al., "Clinical Utility of Plasma Glypican-3 and Osteopontin as Biomarkers of Hepatocellular Carcinoma", Gut and Liver, Mar. 2014, vol. 8, No. 2, pp. 177-185.
Xiao-Fei Liu et al., "Diagnostic accuracy of serum glypican-3 for hepatocellular carcinoma: A systematic review and meta-analysis", Clinical Biochemistry 47, 2014, pp. 196-200.
Cheng Xu et al., "A comparison of glypican-3 with alpha-fetoprotein as a serum marker for hepatocellular carcinoma: a meta-analysis", J Cancer Res Clin Oncol, 2013, vol. 139, pp. 1417-1424.
Min Chen et al., "Reevaluation of glypican-3 as a serological marker for hepatocellular carcinoma", Clinica Chimica Acta vol. 423, 2013, pp. 105-111.
Hasan Ozkan et al., "Diagnostic and Prognostic Role of Serum Glypican 3 in Patients With Hepatocellular Carcinoma", Journal of Clinical Laboratory Analysis 25, 2011, pp. 350-353.
Min Yao et al., "Oncofetal antigen glypican-3 as a promising early diagnostic marker for hepatocellular carcinoma", Hepatobiliary Pancreat Dis Int, Jun. 15, 2011, vol. 10, No. 3, pp. 289-294.
Masahiro Suzuki et al., "Up-regulation of Glypican-3 in Human Hepatocellular Carcinoma", Anticancer Research 30, 2010, pp. 5055-5061.
Hui Liu et al., "Diagnostic value of glypican-3 in serum and liver for primary hepatocellular carcinoma", World Journal of Gastroenterology, Sep. 21, 2010, vol. 16, Issue. 35, pp. 4410-4415.
Qianyun Zhang et al., "Development of a competitive radioimmunoassay for glypican-3 and the clinical application in diagnosis of hepatocellular carcinoma", Clinical Biochemistry 43, 2010, pp. 1003-1008.
Eisuke Yasuda et al., "Evaluation for clinical utility of GPC3, measured by a commercially available Elisa kit with Glypican-3 (GPC3) antibody, as a serological and histological marker for hepatocellular carcinoma", Hepatology Research, 2010, vol. 40, pp. 477-485.
Pisit Tangkijvanich et al., "Diagnostic role of serum glypican-3 in differentiating hepatocellular carcinoma from non-malignant chronic liver disease and other liver cancers", Journal of Gastroenterology and Hepatology vol. 25, 2010, pp. 129-137.
Gary Beale et al., "AFP, PIVKAII, GP3, SCCA-I and follisatin as surveillance biomarkers for hepatocellular cancer in non-alcoholic and alcoholic fatty liver disease", BMC Cancer, 2008, vol. 8, No. 200, 8 pgs. total.
Yoshiaki Ikuta et al., "Highly Sensitive Detection of Melanoma at an Early Stage Based on the Increased Serum Secreted Protein Acidic and Rich in Cysteine and Glypican-3 Levels", Clin Cancer Res, Nov. 15, 2005, vol. 11, No. 22, pp. 8079-8088.
Tetsuya Nakatsura et al., "Identification of Glypican-3 as a Novel Tumor Marker for Melanoma", Clinical Cancer Research, Oct. 1, 2004, vol. 10, pp. 6612-6621.
Mary M Bendig, "Humanization of Rodent Monoclonal Antibodies by CDR Grafting", Methods: A Companion to Methods in Enzymology 8, 1995, pp. 83-93.
Yoshitaka Hippo et al., "Identification of Soluble $NH_2$-Terminal Fragment of Glypican-3 as a Serological Marker for Early-Stage Hepatocellular Carcinoma", Cancer Research 64, Apr. 1, 2004, pp. 2418-2423.
R.J. Wall, "Transgenic Livestock: Progress and Prospects for the Future", Theriogenology 45, 1996, pp. 57-68.
Louis-Marie Houdebine, "Production of pharmaceutical proteins from transgenic animals", Journal of Biotechnology 34, 1994, pp. 269-287.
William E. Paul, M.D., Fundamental Immunology Third Edition, Structure and Function of Immunoglobulins, 1993, pp. 292-295 (6 pgs. total).
Catherine A. Kappel et al., "Regulating gene expression in transgenic animals", Current Opinion in Biotechnology, 1992, vol. 3, pp. 548-553.
Office Action dated Jan. 19, 2017, issued by the U.S. Patent and Trademark Office in U.S. Appl. No. 14/713,416.
Communication, dated Jul. 19, 2017, issued by the Indian Patent Office in counterpart Indian Patent Application No. 1929/CHENP/2006.
Lage et al., "Expression of a glypican-related 62-kDa antigen is decreased in hepatocellular carcinoma in correspondence to the grade of tumor differentiation", Virchows Arch, 2001, vol. 438, pp. 567-573.
Sung et al.,"Glypican-3 is overexpressed in human hepatocellular carcinoma", Cancer Sci, 2003, vol. 94, No. 3, pp. 259-262.
Portolano et al., "Lack of Promiscuity in Autoantigen-Specific H and L Chain Combinations as Revealed by Human H and L Chain Roulette", The Journal of Immunology, 1993, vol. 150, No. 3, pp. 880-887.
Capurro et al., Glypican-3: A Novel Serum and Histochemical Marker for Hepatocellular Carcinoma, Gastroenterology, 2003, vol. 125, pp. 89-97.
Midorikawa et al., Glypican-3, Overexpressed in Hepatocellular Carcinoma, Modulates FGF2 and BMP-7 Signaling, Int. J. Cancer, 2003, vol. 103, pp. 455-465.
Communication dated Jun. 22, 2016, from the European Patent Office in counterpart European application No. 15153329.6.
Notice of Allowance dated Oct. 27, 2016, from the Russian Patent Office in corresponding Russian application No. 2011 115 845/10.
Communication, dated Oct. 16, 2017, issued by the State Intellectual Property Office of the P.R.C. in Application No. 201480071111.X.
Communication, dated Oct. 16, 2017, issued by the United States Patent and Trademark Office in U.S. Appl. No. 14/441,551.
Communication, dated Oct. 16, 2017, issued by the Intellectual Property Office of Singapore in Application No. 11201609014T.
Communication, dated Nov. 28, 2017, issued by the European Patent Office in Application No. 15789676.2.
Fischer et al., "The anti-lymphoma effect of antibody-mediated immunotherapy is based on an increased degranulation of peripheral blood natural killer (NK) cells," Experimental Hematology, vol. 34, No. 6, 2006, pp. 753-759.
Ofuji et al., Consensus of Cancer Therapy, vol. 12, No. 2, 2013, pp. 114-116. (4 pages total).
Takai et al., "Histopathological analyses of the antitumor activity of anti-glypican-3 antibody (GC33) in human liver cancer xenograft models: The contribution of macrophages," Cancer Biology & Therapy, vol. 8, No. 10, May 15, 2009, pp. 930-938.
Yen et al., "Randomized phase II trial of intravenous RO5137382/GC33 at 1600 mg every other week and placebo in previously treated patients with unresectable advanced hepatocellular carcinoma (HCC; NCT01507168)," Journal of Clinical Oncology, vol. 32, No. 15, May 20, 2014, p. 4102. (Abstract).
Abou-Alfa et al., "Randomized phase II placebo controlled study of codrituzumab in previously treated patients with advanced hepatocellular carcinoma," Journal of Hepatology, vol. 65, No. 2, 2016, pp. 289-295.
International Search Report dated Sep. 20, 2016, issued by the International Searching Authority in application No. PCT/JP2016/069493.
Kawaida et al., "Clinicopathological significance of the expression of Glypican-3 in hepatocellular carcinoma", Proceedings of the Japanese Society of Pathology, 104th conference of the Japanese Society of Pathology-Nagoya Congress Center, Mar. 23, 2015, vol. 104, No. 1, p. 324 (total 4 pages).
Ikeda et al., "Japanese phase I study of GC33, a humanized antibody against glypican-3 for advanced hepatocellular carcinoma," Cancer Science, Apr. 2014, vol. 105, No. 4, pp. 455-462.

(56) References Cited

OTHER PUBLICATIONS

Endo, "A novel molecular targeted therapy, humanized anti-glypican 3 anitbody (GC33), for the treatment of unresectable hepatocellular cancer", Medical Science Digest, vol. 39 (9), Aug. 2013, pp. 440-443 (10 pages total).
Hashiguchi et al., "Using immunofluorescent digital slide technology to quantify protein expression in archival paraffin-embedded tissue sections", Pathology International; 2010; vol. 60; pp. 720-725.
Communication dated Jan. 9, 2017 issued by the United States Patent and Trademark Office in U.S. Appl. No. 14/441,551.
Communication dated Apr. 12, 2017 issued by the Intellectual Property Office of India in counterpart application No. 6501/CHENP/2010.
Nakatsura et al., "Glypican-3, overexpressed specifically in human hepatocellular carcinoma, is a novel tumor marker", Biochemical and Biophysical Research Communications 306, 2003, pp. 16-25, XP-002261242 (10 pages total).
Llovet et al., A Molecular Signature to Discriminate Dysplastic Nodules From Early Hepatocellular Carcinoma in HCV Cirrhosis, Journal of Gastroenterology vol. 131, Issue 6, Dec. 2006, pp. 1758-1767 (10 pages total).
"A Phase I, Open-Label, Multi-center, Dose-escalation Study of Safety, Tolerability, and Pharmacokinetics of GC33 Administered Weekly in Patients With Advanced or Metastatic Hepatocellular Carcinoma (HCC)", Clinical Trials.gov (NCT00746317 on Nov. 16, 2010) (4 pages total).
Office Action, dated May 15, 2018, issued by the United States Patent and Trademark Office in co-pending U.S. Appl. No. 15/309,391.
Communication, dated Apr. 18, 2018, issued by the Brazilian Patent Office in Brazilian Application No. PI0909672-8.
Communication, dated Jun. 19, 2018, issued by the Japanese Patent Office in Japanese Application No. 2015-554492.
Zynger et al., "Glypican 3: A Novel Marker in Testicular Germ Cell Tumors", American Journal of Surgical Pathology, vol. 30 No. 12, Dec. 2006, pp. 1570-1575 (6 pages total).
Ishiguro et al., "Anti-Glypican 3 Antibody as a Potential Antitumor Agent for Human Liver Cancer" Cancer Research, vol. 68, No. 23, Dec. 1, 2008, pp. 9832-9838 (7 pages total).
Colman, "Effects of amino acid sequence changes on antibody-antigen interactions", Research in Immunology, vol. 145, 1994, pp. 33-36 (4 pages total).
United States Patent and Trademark Office, "Guidelines for Examination of Patent Applications Under the 35 U.S.C. 112, 1, Written Description Requirement", Federal Register, vol. 66, No. 4, Jan. 5, 2001, pp. 1099-1111 (13 pages total).
Khantasup et al., "Design and Generation of Humanized Single-chain Fv Derived from Mouse Hybridoma for Potential Targeting Application", Monoclonal Antibodies in Immunodiagnosis and Immunotherapy, vol. 34, No. 6, 2015, pp. 404-417 (14 pages total).
Gluck et al., "Phase I Studies of Interleukin (IL)-2 and Rituximab in B-Cell Non-Hodgkin's Lymphoma: IL-2 Mediated Natural Killer Cell Expansion Correlations with Clinical Response", Clinical Cancer Research, vol. 10, Apr. 1, 2004, pp. 2253-2264 (13 pages total).
Hatjiharissi et al., "Individuals Expressing FcγRIIIA-158 V/V and V/F Show Increased NK Cell Surface Expression of FcgRIIIA (CD16), Rituximab Binding, and Demonstrate Higher Levels of ADCC Activity in Response to Rituximab", Blood, vol. 106, 2005, Abstract 776 (2 pages).
Yamauchi et al., "The glypican 3 oncofetal protein is a promising diagnostic marker for hepatocellular carcinoma", Modern Pathology, vol. 18, 2005, pp. 1591-1598 (8 pages total).
Ed Harlow et al., "Antibodies, A Laboratory Manual", Cold Spring Harbor Laboratory, 1988, pp. 141-142 (total 7 pages).
Giuseppe Pilia et al., "Mutations in GPC3, a glypican gene, cause the Simpson-Golabi-Behmel overgrowth syndrome", Nature Genetics, vol. 12, Mar. 1996, pp. 241-247.

A.I. Semenova, "Monitoring of Treatment Efficacy and Detection of Recurrences Using Biomarkers", Practical Oncology, vol. 12, No. 4, pp. 171-177 (2011), total 13 pages.
Office Action, dated Jan. 9, 2018, issued by the United States Patent and Trademark Office in U.S. Appl. No. 15/288,508.
Office Action, dated Jan. 19, 2018, issued by the United States Patent and Trademark Office in U.S. Appl. No. 15/309,391.
Communication, dated Feb. 8, 2018, issued by the Norwegian Industrial Property Office in Norwegian Patent Application No. 20063539.
Communication, dated Dec. 7, 2017, issued by the Russian Patent and Trademark Office in Russian Patent Application No. 2015129697/15.
Communication, dated Jan. 29, 2018, issued by the Indian Intellectual Property Office in Indian Patent Application No. 2357/CHENP/2010.
Communication, dated Aug. 15, 2018, issued by the United States Patent and Trademark Office in U.S. Appl. No. 14/713,416.
Communication, dated Sep. 5, 2018, issued by the State Intellectual Property Office of People's Republic of China in counterpart Application No. 201580024198.X.
Communication, dated Sep. 21, 2018, issued by the United States Patent and Trademark Office in U.S. Appl. No. 15/288,508.
Kiyotaka Nakano et al., "Anti-glypican 3 antibodies cause ADCC against human hepatocellular carcinoma cells", Biochemical and Biophysical Research Communications, vol. 378, No. 2, 2009, pp. 279-284 (6 pages total).
Juan C. Almagro et al., "Humanization of antibodies", Frontiers in Bioscience, vol. 13, pp. 1619-1633, Jan. 1, 2008 (15 pages total).
Yorita et al., "Prognostic significance of circumferential cell surface immunoreactivity of glypican-3 in hepatocellular carcinoma", Liver International, vol. 21, No. 1, Jan. 1, 2011, pp. 120-131.
Hatjiharissi et al., "Increased natural killer cell expression of CD16, augmented binding and ADCC activity to rituximab among individuals expressing the FcγRIIIa-158 V/V and V/F polymorphism", Blood, vol. 110, No. 7, 2007, pp. 2561-2564.
Li Set al., "Prokaryotic Expression of GPC3/MXR7 and Preparation of Anti-GPC3/MXR7 Antibody", China Journal of Modern Medicine, vol. 13, No. 8, Apr. 30, 2003, pp. 15-17.
Mavilio et al., "Characterization of CD56-/CD16+ natural killer (NK) cells: A highly dysfunctional NK subset expanded in HIV-infected viremic individuals", PNAS, vol. 102, No. 8, Feb. 22, 2005, pp. 2886-2891.
Sun et al., "Suppression of Glypican 3 Inhibits Growth of Hepatocellular Carcinoma Cells through Up-Regulation of TGF-$\beta 2^{1,2}$", Neoplasia, vol. 13, No. 8, Aug. 1, 2011, pp. 735-747 (14 pages).
Capurro M.I. et al; "Overexpression of Glypican-3 in human hepatocellular carcinomas determined by immunohistochemistry using a monoclonal antibody", Proceedings of the American Association for Cancer Research, 93rd Annual Meeting, vol. 43, Apr. 6-10, 2002, p. 219.
Haruyama Y et al., High preoperative levels of serum glypican-3 containing N-terminal subunit are associated with poor prognosis in patients with hepatocellular carcinoma after partial hepatectomy, International Journal of Cancer, vol. 137, No. 7, Oct. 1, 2015, pp. 1643-1651.
Communication, dated Dec. 13, 2018, issued by the Australian Patent Office in application No. 2013365430.
Communication, dated Jan. 9, 2019, issued by the Intellectual Property Office of the P.R.C. in application No. 201610183223.5.
Communication, dated Nov. 15, 2018, issued by the U.S. Patent and Trademark Office in U.S. Appl. No. 15/309,391.
Communication, dated Nov. 7, 2018, issued by the European Patent Office in application No. 14874331.3.
Communication, dated Nov. 7, 2018, issued by the Brazilian Patent Office in application No. PI0617412-4.
Communication, dated Oct. 16, 2018, issued by the Brazilian Patent Office in application No. PI0506125-3.
Communication, dated Oct. 24, 2018, issued by the European Patent Office in application No. 16818042.0.
Communication, dated Sep. 26, 2018, issued by the Mexican Patent Office in application No. MX/a/2015/007714.

(56) References Cited

OTHER PUBLICATIONS

Communication, dated Feb. 7, 2019, issued by the European Patent Office in counterpart European Patent Application No. 14874331.3.

* cited by examiner

Lane 1 ; GPC3 core 50 ng, 2; GPC3 core 500 ng

M; marker, 1; CHO, 2; AW2, 3; AW3, 4; AW5, 5; GPC3

METHOD FOR ASSAYING SOLUBLE GPC3 PROTEIN

CROSS REFERENCE TO RELATED APPLICATIONS

This application is a National Stage of International Application No. PCT/JP2014/003409 filed Jun. 25, 2014, claiming priority based on International Application No. PCT/JP2013/007529 filed Dec. 24, 2013, the contents of all of which are incorporated herein by reference in their entirety.

TECHNICAL FIELD

The present invention relates to a method for assaying soluble GPC3 protein in a test sample, comprising using two different antibodies binding to different epitopes present in the N-terminal region of GPC3 protein.

BACKGROUND ART

Deaths caused by hepatocellular carcinoma account for 600,000 deaths each year and are reportedly ranked the 5th most common cancer-related deaths worldwide (Non Patent Literature 1). Most cases of hepatocellular carcinoma die within 1 year after diagnosis as having the disease. Unfortunately, hepatocellular carcinoma patients are frequently diagnosed at a late stage where the patients rarely respond to therapy capable of curing. Medical procedures including chemotherapy, chemoembolization, cauterization, and proton beam therapy are still insufficiently effective for such patients. Many patients exhibit recurrence of the disease, which proceeds rapidly to an advanced stage with vascular invasion and multisite intrahepatic metastasis, resulting in its 5-year survival rate of only 7% (Non Patent Literature 2). Hepatocellular cancer patients with resectable local tumors have relatively good prognosis, but have a 5-year survival rate remaining at 15% to 39% (Non Patent Literature 3).

Glypican-3 (GPC3) is frequently expressed at a high level in liver cancer. It is therefore considered that GPC3 may be useful for the identification of GPC3 functions in liver cancer or as a target for the treatment of liver cancer or a target of the diagnosis of liver cancer.

GPC3 is known to be expressed on cell surface and then processed at the particular site by convertase, phospholipase D, or Notum (Non Patent Literature 4). A method for selecting an HCC patient by assaying GPC3 present in the plasma of patients is disclosed (Patent Literature 1) as a method based on such an event. A diagnostic product for liver cancer comprising an antibody binding to an epitope in a secreted form of GPC3 secreted into plasma, or a method for diagnosing liver cancer using the antibody has been developed (Patent Literatures 2 and 3). Also, a diagnostic product for liver cancer comprising an antibody binding to an epitope in an anchored form of GPC3 still present on cell surface after processing in a tissue specimen or the like isolated from a patient, or a method for diagnosing liver cancer using the antibody has been developed (Patent Literature 4). A method for selecting a prostate cancer patient by measuring a GPC3 level in blood is disclosed, in addition to liver cancer (Patent Literature 5).

All references cited herein are as given below. The contents described in these literatures are incorporated herein by reference in their entirety. However, this does not mean that any of these literatures are the prior art relative to the present specification.

CITATION LIST

Patent Literature

Patent Literature 1: WO2003/100429
Patent Literature 2: WO2004/038420
Patent Literature 3: WO2004/023145
Patent Literature 4: WO2009/116659
Patent Literature 5: WO2007/081790

Non Patent Literature

Non Patent Literature 1: Llovet J M, Burroughs A, Bruix J; Lancet (2003), 362, 1907-17
Non Patent Literature 2: Bosch F X, Ribes J, Cleries R; Gastroenterology (2004), 127, S5-16
Non Patent Literature 3: Takenaka K, Kawahara N, Yamamoto K, Kajiyama K, Maeda T, Itasaka H, Shirabe K, Nishizaki T, Yanaga K, Sugimachi K; Arch Surg (1996), 131, 71-6
Non Patent Literature 4: Cheng A L, Chen Z, Tsao C J, Qin S, Kim J S, et al. Efficacy and safety of sorefanib in patients in the Asia-Pacific region with advanced hepatocellular carcinoma: a phase III randomized, double-blind, placebo-controlled trial. Lancet Oncol. (2009) 10, 25-34

SUMMARY OF INVENTION

Technical Problem

No conventional technique is capable of detecting or accurately quantifying a low concentration of soluble GPC3 contained in a healthy subject body fluid. Therefore, early detection at an initial stage in the development of cancer, selection of an anticancer agent used, or post-treatment prognosis cannot be precisely carried out.

An object of the present invention is to provide a highly sensitive assay method for soluble GPC3 capable of quantitatively measuring the concentration of soluble GPC3 contained in a healthy subject body fluid.

Solution to Problem

The present inventors have conducted diligent studies to attain the object and consequently found that soluble GPC3 protein in a test sample can be assayed highly sensitively by using two different antibodies binding to different epitopes present in the N-terminal region of GPC3 protein.

Specifically, the present invention relates to the following [1] to [12]:

[1] A method for assaying soluble GPC3 protein in a test sample, comprising using two different antibodies binding to different epitopes contained in an amino acid sequence from position 128 to position 357 of GPC3 protein represented by SEQ ID NO: 70;

[2] The assay method according to [1], wherein one of the different epitopes is an epitope comprising at least one amino acid selected from amino acids at positions 337, 339, 340, and 344 of the GPC3 protein;

[3] The assay method according to [1] or [2], wherein one of the different epitopes is an epitope comprising at least one amino acid selected from amino acids at positions 221, 298, 301, 302, 305, 308, and 309 of the GPC3 protein;

[4] The assay method according to [1], wherein the different epitopes are the following combination (A) or (B):
(A) one of the different epitopes is an epitope comprising at least one amino acid selected from amino acids at positions 341, 343, 346, 347, 348, 349, and 350 of the GPC3 protein, and the other epitope is an epitope comprising at least one amino acid selected from amino acids at positions 297, 300, 304, 306, 311, 312, 313, 314, and 315 of the GPC3 protein; and (B) one of the different epitopes is an epitope comprising at least one amino acid selected from amino acids at positions 128, 129, 131, 132, 133, 134, 135, 171, 208, 209, 210, 211, 212, 214, 215, 218, 322, 325, 326, 328, 329, 330, 332, 333, 335, 336, and 338 of the GPC3 protein, and the other epitope is an epitope comprising at least one amino acid selected from amino acids at positions 220, 228, 231, 232, 235, 291, 294, and 295 of the GPC3 protein;

[5] The assay method according to [1], wherein the different epitopes are the following combination (A) or (B):

(A) one of the different epitopes is an epitope comprising at least one amino acid selected from amino acids at positions 337, 339, 340, and 344 of the GPC3 protein and comprising at least one amino acid selected from amino acids at positions 341, 343, 346, 347, 348, 349, and 350 thereof, and the other epitope is an epitope comprising at least one amino acid selected from amino acids at positions 221, 298, 301, 302, 305, 308, and 309 of the GPC3 protein and comprising at least one amino acid selected from amino acids at positions 297, 300, 304, 306, 311, 312, 313, 314, and 315 thereof; and (B) one of the different epitopes is an epitope comprising at least one amino acid selected from amino acids at positions 337, 339, 340, and 344 of the GPC3 protein and comprising at least one amino acid selected from amino acids at positions 128, 129, 131, 132, 133, 134, 135, 171, 208, 209, 210, 211, 212, 214, 215, 218, 322, 325, 326, 328, 329, 330, 332, 333, 335, 336, and 338 thereof, and the other epitope is an epitope comprising at least one amino acid selected from amino acids at positions 221, 298, 301, 302, 305, 308, and 309 of the GPC3 protein and comprising at least one amino acid selected from amino acids at positions 220, 228, 231, 232, 235, 291, 294, and 295;

[6] The assay method according to [1], wherein the different epitopes are an epitope that is bound by an antibody having a heavy chain variable region comprising a sequence having 80% or higher homology to the sequence represented by SEQ ID NO: 38 and a light chain variable region comprising a sequence having 80% or higher homology to the sequence represented by SEQ ID NO: 39, and an epitope that is bound by an antibody having a heavy chain variable region comprising a sequence having 80% or higher homology to the sequence represented by SEQ ID NO: 40 and a light chain variable region comprising a sequence having 80% or higher homology to the sequence represented by SEQ ID NO: 41, or an epitope that is bound by an antibody having a heavy chain variable region comprising a sequence having 80% or higher homology to the sequence represented by SEQ ID NO: 44 and a light chain variable region comprising a sequence having 80% or higher homology to the sequence represented by SEQ ID NO: 45, and an epitope that is bound by an antibody having a heavy chain variable region comprising a sequence having 80% or higher homology to the sequence represented by SEQ ID NO: 42 and a light chain variable region comprising a sequence having 80% or higher homology to the sequence represented by SEQ ID NO: 43;

[7] The assay method according to [1], wherein the two different antibodies are a combination of an antibody having CDR regions identical to CDR regions contained in a heavy chain variable region shown in SEQ ID NO: 38 and CDR regions contained in a light chain variable region shown in SEQ ID NO: 39, and an antibody having CDR regions identical to CDR regions contained in a heavy chain variable region shown in SEQ ID NO: 40 and CDR regions contained in a light chain variable region shown in SEQ ID NO: 41, or a combination of an antibody having CDR regions identical to CDR regions contained in a heavy chain variable region shown in SEQ ID NO: 44 and CDR regions contained in a light chain variable region shown in SEQ ID NO: 45, and an antibody having CDR regions identical to CDR regions contained in a heavy chain variable region shown in SEQ ID NO: 42 and CDR regions contained in a light chain variable region shown in SEQ ID NO: 43;

[8] The assay method according to [7], wherein the CDR regions are CDR1, CDR2, and CDR3 regions based on the Kabat numbering;

[9] The assay method according to [1], wherein the two different antibodies are a combination of an antibody having a heavy chain variable region whose CDR1, CDR2, and CDR3 comprise the amino acid sequences represented by SEQ ID NOs: 46, 47, and 48, respectively, and having a light chain variable region whose CDR1, CDR2, and CDR3 comprise the amino acid sequences represented by SEQ ID NOs: 49, 50, and 51, respectively, and an antibody having a heavy chain variable region whose CDR1, CDR2, and CDR3 comprise the amino acid sequences represented by SEQ ID NOs: 52, 53, and 54, respectively, and having a light chain variable region whose CDR1, CDR2, and CDR3 comprise the amino acid sequences represented by SEQ ID NOs: 55, 56, and 57, respectively, or a combination of an antibody having a heavy chain variable region whose CDR1, CDR2, and CDR3 comprise the amino acid sequences represented by SEQ ID NOs: 58, 59, and 60, respectively, and having a light chain variable region whose CDR1, CDR2, and CDR3 comprise the amino acid sequences represented by SEQ ID NOs: 61, 62, and 63, respectively, and an antibody having a heavy chain variable region whose CDR1, CDR2, and CDR3 comprise the amino acid sequences represented by SEQ ID NOs: 64, 65, and 66, respectively, and having a light chain variable region whose CDR1, CDR2, and CDR3 comprise the amino acid sequences represented by SEQ ID NOs: 67, 68, and 69, respectively;

[10] The assay method according to [1], wherein the two different antibodies are a combination of an antibody having a heavy chain variable region shown in SEQ ID NO: 38 and a light chain variable region shown in SEQ ID NO: 39, and an antibody having a heavy chain variable region shown in SEQ ID NO: 40 and a light chain variable region shown in SEQ ID NO: 41, or a combination of an antibody having a heavy chain variable region shown in SEQ ID NO: 44 and a light chain variable region shown in SEQ ID NO: 45, and an antibody having a heavy chain variable region shown in SEQ ID NO: 42 and a light chain variable region shown in SEQ ID NO: 43;

[11] The assay method according to any one of [1] to [10], wherein any one of the two different antibodies is bound with a magnetic particle; and

[12] The assay method according to any one of [1] to [11], wherein the test sample is a tissue sample, a whole blood sample, a plasma sample, or a serum sample isolated from a human.

Advantageous Effects of Invention

According to the present invention, soluble GPC3 protein in a test sample can be assayed conveniently and highly sensitively by using two different antibodies binding to different epitopes present in the N-terminal region of GPC3 protein. As a result, early detection at an initial stage in the development of cancer, selection of an anticancer agent used, and post-treatment prognosis can be precisely carried out.

DESCRIPTION OF EMBODIMENTS

Definition

Figure 1:
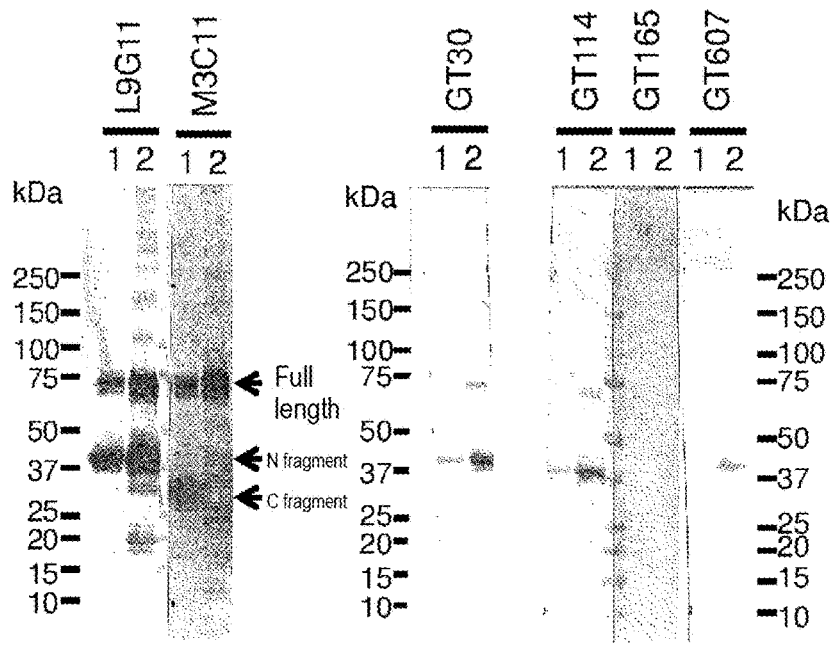
FIG. 1 shows results of subjecting mouse antibodies obtained by screening to Western blotting for GPC3 and a C fragment and N fragment thereof under reductive conditions.

In the present specification, the chemical terms and the technical terms used in relation to the present invention have meanings that are generally understood by those skilled in the art, unless otherwise specified.

Indefinite Article

In the present invention, the indefinite article "a" or "an" refers to one or two or more (i.e., at least one) grammatical subject(s) of the indefinite article. For example, "a factor" means one factor or two or more factors.

Amino Acid

In the present specification, each amino acid is indicated by a one-letter or three-letter code, or both, as indicated by, for example, Ala/A, Leu/L, Arg/R, Lys/K, Asn/N, Met/M, Asp/D, Phe/F, Cys/C, Pro/P, Gln/Q, Ser/S, Glu/E, Thr/T, Gly/G, Trp/W, His/H, Tyr/Y, Ile/I, or Val/V.

Alteration of Amino Acid

A method known in the art such as site-directed mutagenesis (Kunkel et al., Proc. Natl. Acad. Sci. USA (1985) 82, 488-492) or overlap extension PCR can be appropriately adopted for the alteration of an amino acid in the amino acid sequence of an antigen-binding molecule. A plurality of methods known in the art can also be adopted as alteration methods for amino acids to be substituted by amino acids other than natural amino acids (Annu. Rev. Biophys. Biomol. Struct. (2006) 35, 225-249; and Proc. Natl. Acad. Sci. U.S.A. (2003) 100 (11), 6353-6357). For example, a cell-free translation system (Clover Direct (Protein Express Co., Ltd.)) is preferably used which contains tRNA in which a non-natural amino acid is bound with amber suppressor tRNA complementary to a stop codon UAG (amber codon).

In the present specification, the term "and/or" used for indicating an amino acid alteration site includes every combination in which "and" and "or" are appropriately combined. Specifically, the phrase "amino acids at positions 43, 52, and/or 105 are substituted" includes the following variations of amino acid alteration:
(a) position 43, (b) position 52, (c) position 105, (d) positions 43 and 52, (e) positions 43 and 105, (f) positions 52 and 105, and (g) positions 43, 52, and 105.

Numbering of CDR

In the present invention, the amino acid positions assigned to antibody CDRs can be specified according to a method known in the art and can be specified according to, for example, Kabat (Sequences of Proteins of Immunological Interest, National Institute of Health, Bethesda, Md., 1987 and 1991).

Test Sample

In the present invention, the term "test sample" refers to a sample of a tissue or fluid isolated from a subject. In a non-limiting embodiment, examples of such a sample include plasma, serum, spinal fluid, lymph, external sections of the skin, the respiratory tract, the intestinal tract, and the genitourinary tract, tear, saliva, sputum, milk, urine, whole blood or any blood fraction, blood derivatives, blood cells, tumors, nervous tissues, organs or any type of tissue, any sample obtained by lavage (e.g., samples derived from the bronchi), and samples of components constituting cell cultures in vitro.

The concentration of soluble GPC3 can be measured in a biological sample (test sample) isolated from a patient. For example, the concentration of soluble GPC3 can be measured in a sample of whole blood or a sample of a blood fraction such as serum or plasma (in the present specification, also referred to as a whole blood sample, a serum sample, or a plasma sample, respectively). In a non-limiting embodiment, the concentration of soluble GPC3 in the whole blood sample, the serum sample, or the plasma sample of a patient can be measured using, for example, commercially available Human Glypican-3 ELISA kit (Bio-Mosaic Inc.) or Enzyme-linked Immunosorbent Assay Kit For Glypican 3 (GPC3) (USCN Life Science Inc.) and an EDTA-treated whole blood sample, serum sample, or plasma sample.

The term "isolated" refers to causing "artificial" change from a natural state, i.e., shifting and/or removing a naturally occurring substance from its original environment. In the present invention, the term "isolated" means that, for example, a polynucleotide or a polypeptide present in an organism is unisolated, whereas the same polynucleotide or polypeptide thereas is isolated when separated from a material present with the polynucleotide or the polypeptide in a natural state. A polynucleotide or a polypeptide transferred to an organism by transformation, genetic manipulation, or any other recombination method is in an isolated state even if present in the organism (regardless of being alive or dead).

Soluble GPC3

In the present invention, the "soluble GPC3" refers to a soluble form of GPC3 unanchored to GPC3-expressing cells and includes fragments of a secreted form of GPC3 that can be easily dissociated from GPC3 anchored to GPC3-expressing cells under particular conditions in vivo or in vitro. In a non-limiting embodiment, examples of the "soluble GPC3" can include a polypeptide from the amino terminus to position 358 in GPC3 defined by SEQ ID NO: 70, a polypeptide from the amino terminus to position 374 in GPC3 defined by SEQ ID NO: 70, a GPC3 polypeptide liberated by the degradation of a GPI anchor present at the carboxy terminus, and their fragments (Patent Literature 2). Those skilled in the art can appropriately select an approach known in the art for determining the structure of soluble GPC3. In a non-limiting embodiment, a method therefor that may be appropriately used which involves, for example, directly detecting soluble GPC3 present in the serum or the plasma of a patient or a model animal by the method described in Patent Literature 2 and analyzing its structure, or which involves, for example, allowing an enzyme dissociating soluble GPC3, such as convertase, phospholipase D, or Notum, to act on GPC3 expressed in cells cultured in vitro, detecting the resulting soluble GPC3, and analyzing its structure (e.g., J. Cell. Biol. (2003) 163 (3), 625-635).

Method for Measuring Soluble GPC3 Concentration

In the present invention, the soluble GPC3 concentration is measured by an immunological method using two different antibodies binding to different epitopes contained in an amino acid sequence from position 128 to position 357, preferably position 219 to position 357. Also, a method which involves detecting a fragment of soluble GPC3 further digested with an appropriate enzyme may be appropriately adopted.

Preferred examples of the method for assaying soluble GPC3 include enzyme immunoassay (ELISA or EIA), fluorescence immunoassay (FIA), radioimmunoassay (RIA), luminescence immunoassay (LIA), immunoenzymatic technique, fluorescent antibody technique, immunochromatography, immunoturbidimetry, latex turbidimetry, and latex agglutination assay. In the immunological method of the present invention, the soluble GPC3 can be assayed by procedures of manual operation or using an apparatus such as an analyzer.

The immunological method according to the present invention can be carried out according to a method known in the art, for example, sandwich technique. For example, a first antibody immobilized on a carrier, a biological sample, and a second antibody modified with a labeling material are reacted simultaneously or sequentially. This reaction forms a complex of the first antibody immobilized on a carrier, soluble GPC3, and the second antibody modified with a labeling material. The labeling material conjugated with the second antibody contained in this complex can be quantified to measure the amount (concentration) of the soluble GPC3 contained in the biological sample.

In the case of, for example, the enzyme immunoassay, a first antibody-immobilized microplate, serially diluted biological samples, a second antibody modified with an enzyme such as HRP, a washing buffer, and a solution containing a substrate reactive with the enzyme such as HRP are preferably used. In a non-limiting embodiment, the assay can involve reacting the enzyme modifying the second antibody under the optimum conditions thereof with the substrate, and measuring the amount of the resulting enzymatic reaction product by an optical method or the like. In the case of the fluorescence immunoassay, a first antibody-immobilized optical waveguide, serially diluted biological samples, a second antibody modified with a fluorescent material, and a washing buffer can be preferably used. In a non-limiting embodiment, the assay can involve irradiating the fluorescent material modifying the second antibody with excitation light to emit fluorescence, the intensity of which is then measured.

The radioimmunoassay involves measuring the amount of radiation from a radioactive substance. The luminescence immunoassay involves measuring luminescence intensity derived from a luminescent reaction system. For example, the immunoturbidimetry, the latex turbidimetry, or the latex agglutination assay involves measuring transmitted light or scattering light by an endpoint or rate method. The immunochromatography, for example, which is based on visual observation, involves visually measuring the color of the labeling material appearing on a test line. Alternatively, an instrument such as an analyzer may be appropriately used instead of this visual measurement.

In the immunological method of the present invention, the first antibody to be immobilized on a carrier can be adsorbed or bound to the carrier by a method such as physical adsorption, chemical binding, or a combination thereof. A method known in the art can be appropriately used as the method for immobilizing the antibody by physical adsorption. Examples thereof include a method which involves contacting the antibody with the carrier by mixing in a solution such as a buffer solution, and a method which involves contacting the antibody dissolved in a buffer or the like with the carrier. Alternatively, the antibody may be immobilized onto the carrier by chemical binding. Examples thereof include a method which involves mixing and contacting the antibody and the carrier with a divalent cross-linking reagent such as glutaraldehyde, carbodiimide, imide ester, or maleimide to react the reagent with amino groups, carboxyl groups, thiol groups, aldehyde groups, hydroxy groups, or the like in both of the antibody and the carrier. Such immobilization may require treatment for suppressing nonspecific reaction or the natural aggregation or the like of the antibody-immobilized carrier. In such a case, the aftertreatment of the immobilization can be carried out by a method known in the art. Examples thereof include a method which involves coating the surface or the inner wall of the antibody-immobilized carrier by contact with, for example, a protein (e.g., bovine serum albumin (BSA), casein, gelatin, egg albumin, or a salt thereof), a surfactant, or skimmed milk.

In the immunological method of the present invention, the second antibody to be modified with a labeling material can be adsorbed or bound to the labeling material by a method such as physical adsorption, chemical binding, or a combination thereof. A method known in the art can be appropriately used as the method for binding the labeling material to the antibody by physical adsorption. Examples of thereof include a method which involves contacting the antibody with the labeling material by mixing in a solution such as a buffer solution, and a method which involves contacting the antibody dissolved in a buffer or the like with the labeling material. When the labeling material is, for example, gold colloid or latex, the physical adsorption method is effective. The antibody can be mixed and contacted with the gold colloid in a buffer to obtain a gold colloid-labeled antibody. Alternatively, the antibody may be modified with the labeling material by chemical binding. Examples thereof include a method which involves contacting and mixing the antibody and the labeling material with a divalent cross-linking reagent such as glutaraldehyde, carbodiimide, imide ester, or maleimide to react the reagent with amino groups, carboxyl groups, thiol groups, aldehyde groups, hydroxy groups, or the like in both of the antibody and the labeling material. When the labeling material is, for example, a fluorescent material, an enzyme, or a chemiluminescent material, the chemical binding method is effective. Such modification may require treatment for suppressing nonspecific reaction or the natural aggregation or the like of the antibody modified with the labeling material. In such a case, the aftertreatment of the labeling can be carried out by a method known in the art. Examples thereof include a method which involves coating the labeling material-bound antibody by contacting with, for example, a protein (e.g., bovine serum albumin (BSA), casein, gelatin, egg albumin, or a salt thereof), a surfactant, or skimmed milk.

For example, peroxidase (POD), alkaline phosphatase (ALP), β-galactosidase, urease, catalase, glucose oxidase, lactate dehydrogenase, or amylase can be used as the labeling material for the enzyme immunoassay. For example, fluorescein isothiocyanate, tetramethylrhodamine isothiocyanate, substituted rhodamine isothiocyanate, dichlorotriazine isothiocyanate, cyanine, or merocyanine can be used for the fluorescence immunoassay. For example, tritium, iodine 125, or iodine 131 can be used for the radioimmunoassay. For example, a luminol system, a luciferase system, an acridinium ester system, or a dioxetane compound system can be used for the luminescence immunoassay. Also, fine particles made of a material such as polystyrene, a styrene-styrene sulfonate copolymer, an acrylonitrile-butadiene-styrene copolymer, a vinyl chloride-acrylic acid ester copolymer, a vinyl acetate-acrylic acid copolymer, polyacrolein, a styrene-methacrylic acid copolymer, a styrene-glycidyl (meth)acrylate copolymer, a styrene-butadiene copolymer, a methacrylic acid polymer, an acrylic acid polymer, latex, gelatin, liposome, a microcapsule, silica, alumina, carbon black, a metal compound, a metal, a metal colloid, a ceramic, or a magnetic substance can be used for the immunochromatography, the immunoturbidimetry, the latex turbidimetry, or the latex agglutination assay.

A solid-phase carrier in the form of, for example, beads, a microplate, a test tube, a stick, a membrane, or a test pieces made of a material such as polystyrene, polycarbonate, polyvinyltoluene, polypropylene, polyethylene, polyvinyl chloride, nylon, polymethacrylate, polyacrylamide, latex, liposome, gelatin, agarose, cellulose, Sepharose, glass, a metal, a ceramic, or a magnetic substance can be appropriately used as the carrier in the immunological method of the present invention. Particularly, a magnetic substance such as magnetic particles is preferred. Polymer particles containing a magnetic substance or a superparamagnetic substance are preferred as the magnetic particles. Magnetic particles are more preferred in which a magnetic substance layer containing at least one of $Fe_2O_3$ and $Fe_3O_4$ is formed on the surface of a core particle and a polymer layer is further formed on the magnetic substance layer.

Two Different Antibodies

The "two different antibodies" used in the present invention bind to "different epitopes" contained in an amino acid region from position 128 to position 357 of GPC3. The "different epitopes" are not particularly limited as long as the different epitopes are in a relationship that does not mutually inhibit the binding of the "two different antibodies" to the soluble GPC3. Specific examples thereof can include a combination of an epitope on GPC3 that is bound by a GT30 antibody described in Examples and an epitope on GPC3 that is bound by a GT607 antibody described therein, and a combination of an epitope on GPC3 that is bound by a GT114 antibody described therein and an epitope on GPC3 that is bound by a GT165 antibody described therein. Examples of such a combination of the different epitopes include a combination of an epitope (for GT30 and GT165) comprising at least one amino acid selected from amino acids at positions 337, 339, 340, and 344 of the GPC3 protein and an epitope (for GT607 and GT114) comprising at least one amino acid selected from amino acids at positions 221, 298, 301, 302, 305, 308, and 309 of the GPC3 protein. Alternative examples thereof include a combination of an epitope (for GT30) comprising at least one amino acid selected from amino acids at positions 343, 346, 347, 348, 349, and 350 of the GPC3 protein and an epitope (for GT607) comprising at least one amino acid selected from amino acids at positions 297, 300, 304, 306, 311, 312, 313, 314, and 315 of the GPC3 protein, and a combination of an epitope (for GT165) comprising at least one amino acid selected from amino acids at positions 128, 129, 131, 132, 133, 134, 135, 171, 208, 209, 210, 211, 212, 214, 215, 218, 322, 325, 326, 328, 329, 330, 332, 333, 335, 336, and 338 of the GPC3 protein and an epitope (for GT114) comprising at least one amino acid selected from amino acids at positions 220, 228, 231, 232, 235, 291, 294, and 295 of the GPC3 protein. Further examples thereof can include a combination of an epitope (for GT30) comprising at least one amino acid selected from amino acids at positions 337, 339, 340, and 344 of the GPC3 protein and comprising at least one amino acid selected from amino acids at positions 341, 343, 346, 347, 348, 349, and 350 thereof, and an epitope (for GT607) comprising at least one amino acid selected from amino acids at positions 221, 298, 301, 302, 305, 308, and 309 of the GPC3 protein and comprising at least one amino acid selected from amino acids at positions 297, 300, 304, 306, 311, 312, 313, 314, and 315 thereof, and a combination of an epitope (for GT165) comprising at least one amino acid selected from amino acids at positions 337, 339, 340, and 344 of the GPC3 protein and comprising at least one amino acid selected from amino acids at positions 128, 129, 131, 132, 133, 134, 135, 171, 208, 209, 210, 211, 212, 214, 215, 218, 322, 325, 326, 328, 329, 330, 332, 333, 335, 336, and 338 thereof, and an epitope (for GT114) comprising at least one amino acid selected from amino acids at positions 221, 298, 301, 302, 305, 308, and 309 of the GPC3 protein and comprising at least one amino acid selected from amino acids at positions 220, 228, 231, 232, 235, 291, 294, and 295 thereof.

The "two different antibodies" are not particularly limited as long as the different antibodies recognize different epitopes in the region described above and are in a relationship that does not mutually inhibit their binding to the soluble GPC3. Specific examples of the "two different antibodies" used in the present invention can include a combination of a GT30 antibody and a GT607 antibody, and a combination of a GT165 antibody and a GT114 antibody.

GT30 Antibody

The GT30 antibody recognizes an epitope comprising at least one amino acid selected from amino acids at positions 337, 339, 340, 341, 344, 343, 346, 347, 348, 349, and 350 of the GPC3 protein. The GT30 antibody has a heavy chain variable region shown in SEQ ID NO: 38 and a light chain variable region shown in SEQ ID NO: 39 and has heavy chain CDR1, heavy chain CDR2, and heavy chain CDR3 comprising the amino acid sequences represented by SEQ ID NO: 46, SEQ ID NO: 47, and SEQ ID NO: 48, respectively, and light chain CDR1, light chain CDR2, and light chain CDR3 comprising the amino acid sequences represented by SEQ ID NO: 49, SEQ ID NO: 50, and SEQ ID NO: 51, respectively (these sequences of CDR1, CDR2, and CDR3 are based on the Kabat numbering).

GT607 Antibody

The GT607 antibody recognizes an epitope comprising at least one amino acid selected from amino acids at positions 221, 298, 301, 302, 305, 308, 309, 297, 300, 304, 306, 311, 312, 313, 314, and 315 of the GPC3 protein. The GT607 antibody has a heavy chain variable region shown in SEQ ID NO: 40 and a light chain variable region shown in SEQ ID NO: 41 and has heavy chain CDR1, heavy chain CDR2, and heavy chain CDR3 comprising the amino acid sequences represented by SEQ ID NO: 52, SEQ ID NO: 53, and SEQ ID NO: 54, respectively, and light chain CDR1, light chain CDR2, and light chain CDR3 comprising the amino acid sequences represented by SEQ ID NO: 55, SEQ ID NO: 56, and SEQ ID NO: 57, respectively (these sequences of CDR1, CDR2, and CDR3 are based on the Kabat numbering).

GT165 Antibody

The GT165 antibody recognizes an epitope comprising at least one amino acid selected from amino acids at positions 337, 339, 340, 344, 128, 129, 131, 132, 133, 134, 135, 171, 208, 209, 210, 211, 212, 214, 215, 218, 322, 325, 326, 328, 329, 330, 332, 333, 335, 336, and 338 of the GPC3 protein. The GT165 antibody has a heavy chain variable region shown in SEQ ID NO: 44 and a light chain variable region shown in SEQ ID NO: 45 and has heavy chain CDR1, heavy chain CDR2, and heavy chain CDR3 comprising the amino acid sequences represented by SEQ ID NO: 58, SEQ ID NO: 59, and SEQ ID NO: 60, respectively, and light chain CDR1, light chain CDR2, and light chain CDR3 comprising the amino acid sequences represented by SEQ ID NO: 61, SEQ ID NO: 62, and SEQ ID NO: 63, respectively (these sequences of CDR1, CDR2, and CDR3 are based on the Kabat numbering).

GT114 Antibody

The GT114 antibody recognizes an epitope comprising at least one amino acid selected from amino acids at positions 221, 298, 301, 302, 305, 308, and 309 of the GPC3 protein and comprising at least one amino acid selected from amino acids at positions 220, 228, 231, 232, 235, 291, 294, and 295 thereof. The GT114 antibody has a heavy chain variable region shown in SEQ ID NO: 42 and a light chain variable region shown in SEQ ID NO: 43 and has heavy chain CDR1, heavy chain CDR2, and heavy chain CDR3 comprising the amino acid sequences represented by SEQ ID NO: 64, SEQ ID NO: 65, and SEQ ID NO: 66, respectively, and light chain CDR1, light chain CDR2, and light chain CDR3 comprising the amino acid sequences represented by SEQ ID NO: 67, SEQ ID NO: 68, and SEQ ID NO: 69, respectively (these sequences of CDR1, CDR2, and CDR3 are based on the Kabat numbering).

Hereinafter, the nucleotide sequences and the amino acid sequences of the heavy chain and light chain variable regions of each antibody will be described:

```
Nucleotide sequence of GT30 H chain
                                            (SEQ ID NO: 30)
ATGGAATGGATCTGGATCTTTCTCTTCATCCTGTCAGGAACTGCAGGTGT

CCAATCCCAGGTTCAGCTGCAGCAGTCTGGAGCTGAGCTGGCGAGGCCTG

GGGCTTCAGTGAAACTGTCCTGCAGGGCTTCTGGCTACACCTTCACAAGC

TATGGTATAAGCTGGATGATGCAGAGAACTGGACAGGGCCTTGAGTGGAT

TGGAGAGATTTATCCTAGAAGTGGTATTACTTACTACAATGAGAAGTTCA

AGGGCAAGGCCACACTGACTGCAGACAAATCCTCCAGCACAGCCTACATG

CAGCTCAGCAGCCTGACATCTGAGGACTCTGCAGTCTATTTCTGTGCAAG

AGATGTCTCTGATGGTTACCTTTTTCCTTACTGGGGCCAAGGGACTCTGG

TCACTGTCTCTGCAGCCAAA

Nucleotide sequence of GT30 L chain
                                            (SEQ ID NO: 31)
ATGAGTGTGCCCACTCAGGTCCTGGGGTTGCTGCTGCTGTGGCTTACAGG

TGCCAGATGTGACATCCAGATGACTCAGTCTCCAGCCTCCCTATCTGCAT

CTGTGGGAGAAACTGTCACCATCACATGTCGAACAAGTGAGAATATTTAC

AGTTATTTAGCATGGTATCAGCAGAAACAGGGAAAATCTCCTCAGCTCCT

GGTCTATAATGCAAAAACCTTACCAGAAGGTGTGCCATCAAGGTTCAGTG

GCAGTGGATCAGGCACACAGTTTTCTCTGAAGATCAACAGCCTGCAGCCT

GAAGATTTTGGGAGTTATTACTGTCAACATCATTATGGTACTCCTCCGAC

GTTCGGTGGAGGCACCAAGCTGGAAATCAAACGGGCT

Nucleotide sequence of GT607 H chain
                                            (SEQ ID NO: 32)
ATGAACTTCGGGCTCAGCTTGATTTTCCTTGCCCTCATTTTAAAAGGTGT

CCAGTGTGAGGTGCAGCTGGTGGAGTCTGGGGGAGACGTAGTGAGACCTG

GAGGGTCCCTGAAACTCTCCTGTGCAGCCTCTGGATTCACTTTCAGTAGT

TATGGCATGTCCTGGGTTCGCCAGCTTCCAGACAAGAGGCTGGAGTGGGT

CGCAAGTGTTGGTAATGGAGGTAGTTACAGGTACTATCCAGAGAATTTGA

AGGGGCGGTTCACCATCTCCAGAGACAATACCAAGAACACCCTATACCTG

CAAATTAGTGGTCTGAAGTCTGAGGACACAGCCATTTATTACTGTGCAAG

ACGGGGGGCTTTCCCGTACTTCGATGTCTGGGGCGCAGGGACCACGGTCA

CCGTCTCCTCAGCCAAA

Nucleotide sequence of GT607 L chain
                                            (SEQ ID NO: 33)
ATGGATTTTCAAGTGCAGATTTTCAGCTTCCTGCTAATCAGTGCCTCAGT

CATAGTATCCAGAGGACAAATTGTTCTCACCCAGTCTCCAGCAATCATGT

CTGCATCTCCAGGGGAGAAGGTCACCCTGGCCTGCAGTGCCAGCTCAAGT

GTAACTTACATGCACTGGTACCAGCAGAAGTCAGGCACCTCCCCCAAAAG

ATGGATTTATGAAACATCCAAACTGGCTTCTGGAGTCCCTCCTCGCTTCA

GTGGCAGTGGGTCTGGGACCTCTTACTCTCTCACAATCAGCACCATGGAG

GCTGAAGATGCTGCCACTTATTACTGCCAACAGTGGAGTAGTAACCCGCT

CACGTTCGGTGCTGGGACCAAGCTGGAGCTGAAACGGGCT

Nucleotide sequence of GT114 H chain
                                            (SEQ ID NO: 34)
ATGAGAGTGCTGATTCTTTTGTGGCTGTTCACAGCCTTTCCTGGTATCCT

ATCTGATGTGCAGCTTCAGGAGTCGGGACCTGGCCTGGTGAAACCTTCTC

AGTCTCTGTCCCTCACCTGCACTGTCACTGGCTACTCAATCACCAGTGAT

TCTGCCTGGAACTGGATCCGGCAGTTTCCAGGAAACAAACTGGAGTGGAT

GGCCTACATAATGTACAGTGGTATCACTAGCTACAATCCATCTCTCAAAA

GTCGAATCTCTATCACTCGAGACACAGCCAAGAACCAGTTCTTTCTGCAG

TTGAATTCTGTGACTACTGAGGACTCAGCCACATATTACTGTTCACGAGG

CTACTGGTACTTCGATGTCTGGGGCGCAGGGACTACGGTCACCGTCTCCT

CAGCCAAA
```

Nucleotide sequence of GT114 L chain
(SEQ ID NO: 35)
ATGGATTTTCAGGTGCAGATTTTCAGCTTCCTGCTAATCAGTGCCTCAGT
CATAATGTCCAGAGGACAAATTGTTCTCACCCAGTCTCCAGCAATCATGT
CTGCATCTCTAGGGGAGGAGATCACCCTAACCTGCAGTGCCAGCTCGAGT
GTGAGTTACATGCACTGGTACCAGCAGAAGTCAGGCACTTCTCCCAAACT
CTTGATTTATAGCACATCCATCCTGGCTTCTGGAGTCCCTTCTCGCTTCA
GTGGCAGTGGGTCTGGGACCTTTTATTCTCTCACAATCAGCAGTGTGGAG
GCTGAAGATGCTGCCGATTATTACTGCCTTCAGTGGATTACTTATCGGAC
GTTCGGTGGAGGCACCAAGCTGGAAATCAAACGGGCT Nucleotide sequence of GT165 H chain
(SEQ ID NO: 36)
ATGTGTTGGAGCTGTATCATCCTCTTCCTGTTAGCAACAGCTGCACGTGT
GCACTCCCAGGTCCAGCTGCAGCAGTCTGGGGCTGAGCTGGTGGGGCCTG
GGGCCTCAGTGAAGATTTCCTGCAAGGCTTTTGGCTACACCTTCACAAAC
CATCATATAAACTGGGTGAAGCAGAGGCCTGGACAGGGCCTGGACTGGAT
TGGATATATTAATCCTTATAATGATTATACTAACTACAACCAGAAGTTCA
AGGGCAAGGCCACATTGACTGTAGACAAATCCTCCAGCACAGCCTATATG
GAGCTTAGCAGCCTGACATCTGAGGACTCTGCAGTCTATTACTGTGCAAG
ATCAGACCCCGCCTGGTTTGCTTACTGGGGCCAAGGGACTCTGGTCACTG
TCTCTGCAGCCAAA Nucleotide sequence of GT165 L chain
(SEQ ID NO: 37)
ATGAGACCCTCCATTCAGTTCCTGGGGCTCTTGTTGTTCTGGCTTCATGG
TGCTCAGTGTGACATCCAGATGACACAGTCTCCATCCTCACTGTCTGCAT
CTCTGGGAGGCAAAGTCACCATCACTTGCAAGGCAAGCCAAGACATTAAC
AAGAATATAGCTTGGTACCAACACAAGCCTGGAAAAGGTCCTAGGCTGCT
CATATGGTACACATATACATTACAACCAGGCATCCCATCAAGGTTCAGTG
GAAGTGGATCTGGGAGAGATTATTCCTTCAGCATCAGCAACCTGGAGCCT
GAAGATATTGCAACTTATTACTGTCTACAGTATGATAATCTTCCATTCAC
GTTCGGCACGGGGACAAAATTGGAAATAAAACGGGCT Amino acid sequence of GT30 H chain variable region
(SEQ ID NO: 38)
QVQLQQSGAELARPGASVKLSCRASGYTFTSYGISWMMQRTGQGLEWIGE
IYPRSGITYYNEKFKGKATLTADKSSSTAYMQLSSLTSEDSAVYFCARDV
SDGYLFPYWGQGTLVTVSSAK Amino acid sequence of GT30 L chain variable region
(SEQ ID NO: 39)
DIQMTQSPASLSASVGETVTITCRTSENIYSYLAWYQQKQGKSPQLLVYN
AKTLPEGVPSRFSGSGSGTQFSLKINSLQPEDFGSYYCQHHYGTPPTFGG
GTKLEIKRA Amino acid sequence of GT607 H chain variable region
(SEQ ID NO: 40)
EVQLVESGGDVVRPGGSLKLSCAASGFTFSSYGMSWVRQLPDKRLEWVAS
VGNGGSYRYYPENLKGRFTISRDNTKNTLYLQISGLKSEDTAIYYCARRG
AFPYFDVWGAGTTVTVSSAK Amino acid sequence of GT607 L chain variable region
(SEQ ID NO: 41)
QIVLTQSPAIMSASPGEKVTLACSASSSVTYMHWYQQKSGTSPKRWIYET
SKLASGVPPRFSGSGSGTSYSLTISTMEAEDAATYYCQQWSSNPLTFGAG
TKLELKRA Amino acid sequence of GT114 H chain variable region
(SEQ ID NO: 42)
DVQLQESGPGLVKPSQSLSLTCTVTGYSITSDSAWNWIRQFPGNKLEWMA
YIMYSGITSYNPSLKSRISITRDTAKNQFFLQLNSVTTEDSATYYCSRGY
WYFDVWGAGTTVTVSSAK Amino acid sequence of GT114 L chain variable region
(SEQ ID NO: 43)
QIVLTQSPAIMSASLGEEITLTCSASSSVSYMHWYQQKSGTSPKLLIYST
SILASGVPSRFSGSGSGTFYSLTISSVEAEDAADYYCLQWITYRTFGGGT
KLEIKRA Amino acid sequence of GT165 H chain variable region
(SEQ ID NO: 44)
QVQLQQSGAELVGPGASVKISCKAFGYTFTNHHINWVKQRPGQGLDWIGY
INPYNDYTNYNQKFKGKATLTVDKSSSTAYMELSSLTSEDSAVYYCARSD
PAWFAYWGQGTLVTVSSAK Amino acid sequence of GT165 L chain variable region
(SEQ ID NO: 45)
DIQMTQSPSSLSASLGGKVTITCKASQDINKNIAWYQHKPGKGPRLLIWY
TYTLQPGIPSRFSGSGSGRDYSFSISNLEPEDIATYYCLQYDNLPFTFGT
GTKLEIKRA Hereinafter, the CDR sequences of each antibody will be described.

GT30 H chain CDR sequences
CDR1
(SEQ ID NO: 46)
SYGIS

CDR2
(SEQ ID NO: 47)
EIYPRSGITYYNEKFKG

CDR3
(SEQ ID NO: 48)
DVSDGYLFPY

Amino acid sequence of GT30 L chain variable region
CDR1
(SEQ ID NO: 49)
RTSENIYSYLA

CDR2
(SEQ ID NO: 50)
NAKTLPE

CDR3
(SEQ ID NO: 51)
QHHYGTPPT

Amino acid sequence of GT607 H chain variable region
CDR1
(SEQ ID NO: 52)
SYGMS

CDR2
(SEQ ID NO: 53)
SVGNGGSYRYYPENLKG

CDR3
(SEQ ID NO: 54)
RGAFPYFDV

Amino acid sequence of GT607 L chain variable region
CDR1
(SEQ ID NO: 55)
SASSSVTYMH

CDR2
(SEQ ID NO: 56)
ETSKLAS

CDR3
(SEQ ID NO: 57)
QQWSSNPLT

Amino acid sequence of GT165 H chain variable region
CDR1
(SEQ ID NO: 58)
NHHIN

CDR2
(SEQ ID NO: 59)
YINPYNDYTNYNQKFKG

CDR3
(SEQ ID NO: 60)
SDPAWFAY

Amino acid sequence of GT165 L chain variable region (SEQ ID NO: 53)
CDR1
(SEQ ID NO: 61)
KASQDINKNIA

CDR2
(SEQ ID NO: 62)
YTYTLQP

CDR3
(SEQ ID NO: 63)
LQYDNLPFTFGTGTKLEIK

Amino acid sequence of GT114 H chain variable region
CDR1
(SEQ ID NO: 64)
SDSAWN

CDR2
(SEQ ID NO: 65)
YIMYSGITSYNPSLKS

CDR3
(SEQ ID NO: 66)
GYWYFDV

Amino acid sequence of GT114L chain variable region (SEQ ID NO: 51)
CDR1
(SEQ ID NO: 67)
SASSSVSYMH

CDR2
(SEQ ID NO: 68)
STSILAS

CDR3
(SEQ ID NO: 69)
LQWITYRT

For the assay of soluble GPC3 protein according to the present invention, antibodies having heavy chain and light chain variable regions having amino acid sequences with high homology or identity to the amino acid sequences of the heavy chain and light chain variable regions, respectively, of the antibodies described above can be used instead of the antibodies described above. The homology to the amino acid sequences of the heavy chain and light chain variable regions of the antibodies described above is at least 70% or higher, preferably 80% or higher, more preferably, for example, 90%, further preferably 95%, particularly preferably 98% or higher. The homology or the identity (similarity) can be calculated using any well-known algorithm, for example, Needleman-Wunsch, Smith-Waterman, BLAST, or FASTA and is calculated using, for example, the BLAST program (Atschul et al., J. Molec. Biol., 1990; 215: 403-410) under default conditions.

Antibody Recognizing Same Epitopes

A combination of antibodies respectively binding to the same epitopes as those for the antibodies described above can also be used as the "two different antibodies" of the present invention. The antibody binding to the same epitope as that for each antibody can be obtained by using a method known in the art such as competitive ELISA or by assaying competition (cross-reactivity) with each antibody described above for the soluble GPC3 protein or an epitope fragment recognized by this antibody.

Recombinant Antibody

A combination of antibodies each having heavy chain and light chain variable regions identical to those of the GT30 antibody, the GT607 antibody, the GT165 antibody, or the GT114 antibody, or a combination of antibodies each having heavy chain CDR (CDR1, CDR2, and CDR3) and light chain CDR (CDR1, CDR2, and CDR3) regions identical to those of any of these antibodies can also be used as the "two different antibodies" of the present invention. A combination of chimeric antibodies, humanized antibodies, or human antibodies of these antibodies can also be used as the "two different antibodies" of the present invention.

Each antibody having heavy chain and light chain variable regions identical to those of the GT30 antibody, the GT607 antibody, the GT165 antibody, or the GT114 antibody, or each antibody having heavy chain CDRs and light chain CDRs identical to those of any of these antibodies can be prepared by a recombination technique. Specifically, DNAs encoding the heavy chain and light chain variable regions of the anti-GPC3 N-terminal peptide antibody or the anti-GPC3 C-terminal peptide antibody of interest are incorporated into expression vectors having DNAs encoding desired antibody constant regions (C regions), and host cells are transformed with the resulting expression vectors and allowed to express antibodies.

For the antibody gene expression, the antibody heavy chain (H chain)- and light chain (L chain)-encoding DNAs can be separately incorporated into different expression vectors, with which a host cell can be co-transfected. Alternatively, the H chain- and L chain-encoding DNAs may be incorporated into a single expression vector, with which a host cell can be transformed (see WO 94/11523).

In addition to the host cells, transgenic animals can be used for the recombinant antibody production. For example, the antibody gene is inserted to a midpoint in a gene encoding a protein (goat β casein, etc.) specifically produced in milk to prepare a fusion gene. A DNA fragment containing the fusion gene having the antibody gene insert is injected into a goat embryo, which is in turn introduced into a female goat. The desired antibody is obtained from milk produced by transgenic goats (or progeny thereof) brought forth by the goat that has received the embryo. In addition, hormone may be appropriately used for the transgenic goats in order to increase the amount of milk containing the desired antibody produced from the transgenic goats (Ebert, K. M. et al., Bio/Technology (1994) 12, 699-702).

In the present invention, genetically recombinant antibodies that have been engineered artificially, for example, chimeric antibodies (humanized antibodies, etc.) can be used, in addition to the antibodies described above. These engineered antibodies can be produced by use of a known method. In the case of using the antibodies of the present invention as antibodies for treatment, genetically recombinant antibodies are preferably used.

The chimeric antibodies are obtained by linking the antibody V region-encoding DNAs obtained as described above to human antibody C region-encoding DNAs and incorporating the resulting products into expression vectors, which are then transferred to hosts to produce the chimeric antibodies. Chimeric antibodies useful for the present invention can be obtained by this known method.

The humanized antibodies, also called reshaped human antibodies, comprise complementarity determining regions (CDRs) of a non-human animal (e.g., mouse) antibody grafted in human antibodies, and a general genetic recombination method therefor is also known (see European Patent Application Publication No. EP 125023 and WO 96/02576).

The assay method of the present invention is an invention useful for a method for examining the possibility of liver cancer in a test subject by detecting solubilized GPC3 protein in a test sample isolated from the test subject, as with an invention described in, for example, Japanese Patent No. 4283227. Also, the assay method of the present invention is an invention also useful for a drug for predicting or determining recurrence after treatment of liver cancer, containing an anti-GPC3 antibody, as with an invention described in Japanese Patent No. 4658926. The assay method of the present invention can be used in a diagnosis method and a method for predicting or determining recurrence, comprising the assay method of the present invention. As shown later in Examples, the assay method of the present invention is capable of assaying soluble GPC3 protein contained in healthy subject blood on the order of several pg/mL and thus, is a more useful technique for early detection and prognosis of liver cancer as compared with the inventions related to the two patents described above.

More specifically, since the concentration range of soluble GPC3 in healthy subjects is approximately 15 to 174 pg/mL, soluble GPC3 detected at a level exceeding this range indicates the possibility that liver cancer has developed or recurred, and suggests that the risk can be reduced by early detection.

The present invention also provides an assay kit for use in the method for assaying soluble GPC3 protein according to the present invention, comprising the two different antibodies binding to different epitopes. These antibodies may be provided in a state immobilized on the carrier mentioned above or may be provided independently of the carrier. The kit may additionally comprise standard solutions of serially diluted soluble GPC3. Assay principles, etc., for use in the immunological assay kit of the present invention are the same as in the immunological method mentioned above. In the assay kit of the present invention, any of various aqueous solvents may be used as a solvent. Examples of the aqueous solvents include purified water, saline, and various buffers such as tris buffers, phosphate buffers, and phosphate-buffered saline. The pH of this buffer can be appropriately selected from among suitable pHs. The pH value used is not particularly limited and is generally selected within the range of pH 3 to 12.

The assay kit of the present invention may appropriately contain, in addition to the components mentioned above, one or two or more components selected from proteins (e.g., bovine serum albumin (BSA), human serum albumin (HSA), casein, and salts thereof), various salts, various sugars, skimmed milk, various animal sera (e.g., normal rabbit serum), various antiseptics (e.g., sodium azide and antibiotics), activators, reaction accelerants, sensitivity-increasing substances (e.g., polyethylene glycol), nonspecific reaction-inhibiting substances, various surfactants (e.g., nonionic surfactants, amphoteric surfactants, and anionic surfactants), and the like. The concentrations of these components contained in the assay reagent are not particularly limited and are preferably 0.001 to 10% (W/V). Particularly preferred concentrations are appropriately selected within the range of 0.01 to 5% (W/V).

The assay kit of the present invention may be further combined with other reagents, in addition to the components mentioned above. Examples of these other reagents include buffers, diluting solutions for biological samples, reagent diluting solutions, reagents containing labeling materials, reagents containing substances that generate signals such as color, reagents containing substances involved in the generation of signals such as color, reagents containing substances for calibration, and reagents containing substances for accuracy control.

The assay kit of the present invention is not particularly limited by its form and may be provided as an integral-type assay kit comprising all of the components constituting the assay kit of the present invention in order to carry out assay conveniently in a short time. Examples of the integral-type assay kit include ELISA kits, fluorescence immunoassay kits, and immunochromatography kits. The ELISA kit form comprises, for example, a first antibody-immobilized microplate, standard solutions of serially diluted soluble GPC3, a second antibody modified with an enzyme such as HRP, a washing buffer, and a substrate solution for the enzymatic reaction. The fluorescence immunoassay kit comprises, for example, a first antibody-immobilized optical waveguide, standard solutions of serially diluted soluble GPC3, a second antibody modified with a fluorescent material, and a washing buffer. The immunochromatography kit comprises a membrane housed in a reaction cassette where the first antibody is immobilized at one end (downstream) of the membrane. In an exemplary embodiment, a developing solution is placed at the other end (upstream) of the membrane; a pad supplemented with a substrate for the labeling agent is disposed in proximity (downstream) to the developing solution; and a pad supplemented with the second antibody labeled as described above is disposed in the central part of the membrane.

EXAMPLES

Hereinafter, the present invention will be described in detail with reference to Examples. However, the present invention is not intended to be limited by these Examples.

Example 1

A Balb/c or MRL/lpr mice were immunized a total of 6 to 9 times with GPC3 core (sGPC3-His) protein prepared by the C-terminal His tagging of the extracellular domain (positions 25 to 563) of GPC3 core variant derived from human glypican-3 (GPC3; SEQ ID NO: 70) by the exchange of serine at two heparan sulfate-binding sites (positions 495 and 509) to alanine. 3 days after the final immunization, the splenocytes of this mouse were fused with mouse myeloma cells SP2/0 by a routine method using PEG1500 or by using HVJ-E (Ishihara Sangyo Kaisha, Ltd.).

Next, hybridoma cells were screened by ELISA using sGPC3-His directly immobilized on a solid phase, ELISA using sGPC3-His bound with an anti-His antibody immobilized on a solid phase, or Cell ELISA using CHO cells stably expressing GPC3 (see WO 2006/006693).

Example 2

The sGPC3-His protein has been found to yield bands of approximately 86 kDa, approximately 43 kDa, and approximately 33 kDa, which correspond to a full length, a protease-cleaved N-terminal fragment, and a protease-cleaved C-terminal fragment, respectively, in SDS-PAGE under reductive conditions (WO 2006/006693). Mouse antibodies thus obtained by the screening were used in Western blot for sGPC3-His to select antibodies that did not recognize the C-terminal fragment. As a result, GT30, GT114, and GT607 as N-terminal fragment-recognizing antibodies, and GT165 whose recognition site was unidentified were obtained (FIG. 1).

Figure 2:
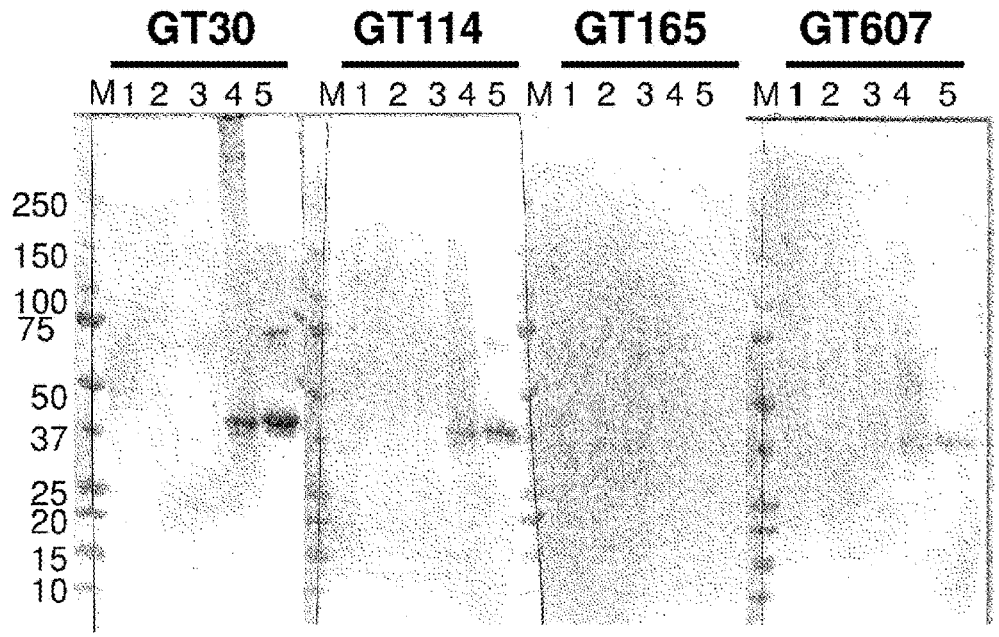
FIG. 2 shows results of subjecting GT30, GT114, GT607, and GT165 antibodies to Western blotting under reduction of pellets of CHO cells expressing either GPC3 or each fragment thereof (AW2, AW3, and AW5).

Subsequently, C-terminally His-tagged recombinant products of positions 1 to 196 (AW2), positions 1 to 218 (AW3), and positions 1 to 357 (AW5) of GPC3 were each expressed in CHO cells, and pellets of the CHO cells expressing each recombinant product were used in Western blot. As a result, as shown in FIG. 2 and Table 1, GT30, GT114, and GT607 were confirmed to have reactivity with AW5 or sGPC3-His, but no reactivity with AW2 and AW3, indicating that these antibodies bind to positions 219 to 357 of GPC3. On the other hand, GT165 was confirmed to have reactivity with none of these products, suggesting the possibility that this antibody strongly recognizes conformation.

TABLE 1

| Clone | Immunized mouse | Isotype | Western blot analysis | | | |
|---|---|---|---|---|---|---|
| | | | sGPC3-His | AW2 (1-196) | AW3 (1-218) | AW5 (1-357) |
| GT114 | BALB/c | IgG1 | ++ | − | − | + |
| GT607 | BALB/c | IgG1 | ++ | − | − | + |
| GT30 | MRL | IgG1 | ++ | − | − | ++ |
| GT165 | MRL | IgG1 | +/− | − | − | − |

Example 3

Figure 3:
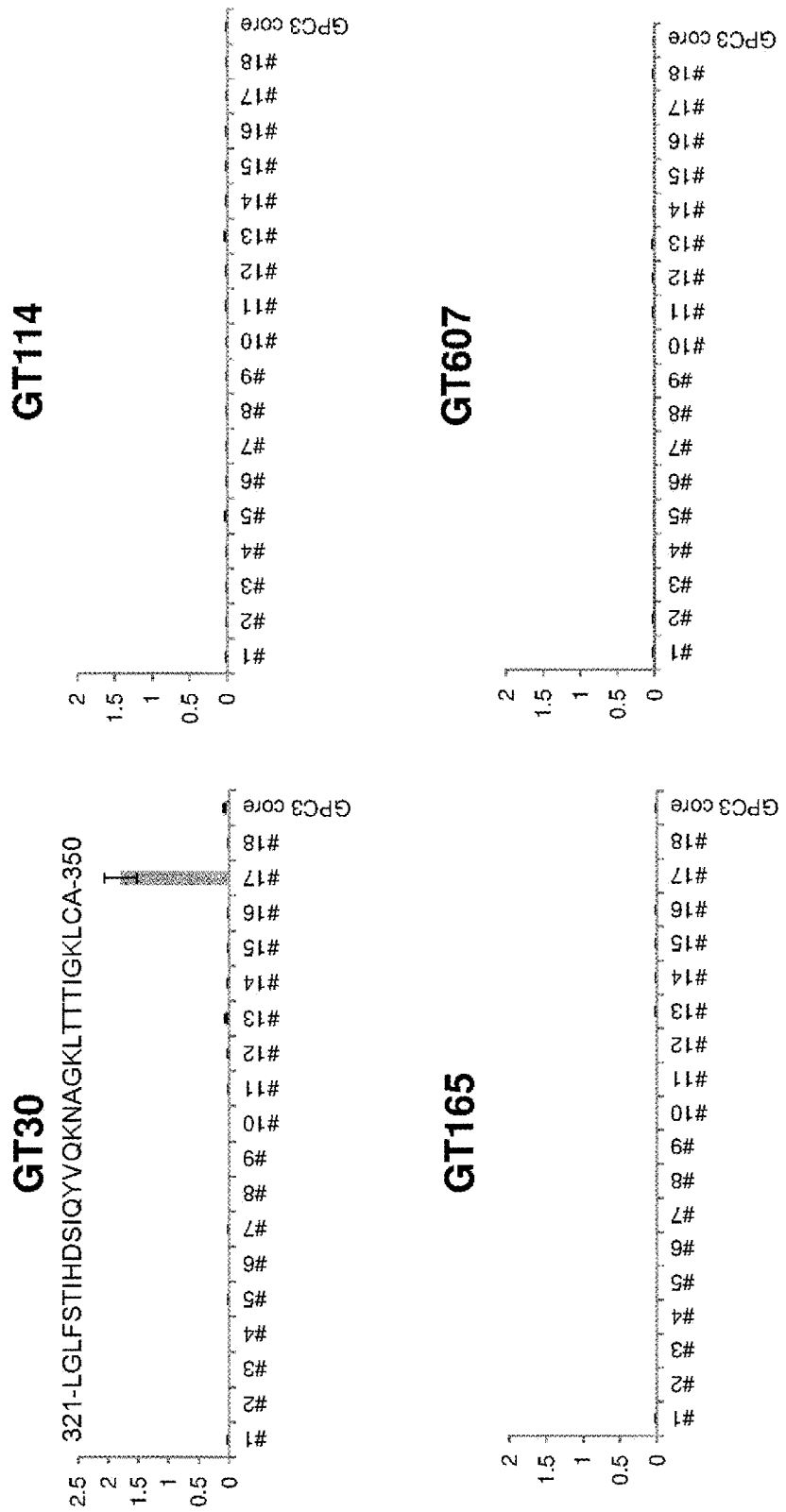
FIG. 3 shows results of a binding test between the GT30, GT114, GT607, or GT165 antibody and each fragment of GPC3.

In order to identify more detailed epitopes for the antibodies, the amino acid sequence of GPC3 was divided into peptides of 30 residues containing 10-residue overlaps, and the corresponding peptides were synthesized (SEQ ID NOs: 1 to 29 in Table 2). Each peptide thus synthesized was dissolved at a concentration of 1 mg/mL in dimethyl sulfoxide and then diluted to 1 μg/mL with PBS. The diluted peptide solution was added at 70 μL/well to a 96-well plate and immobilized thereon at room temperature for 1 hour. After removal of unimmobilized peptides, 20% Blocking-one (Nacalai Tesque, Inc.) was added thereto as a blocking buffer solution at 200 μL/well, and the plate was blocked overnight. After removal of the blocking buffer solution, each well was washed with TBS-T three times, and each antibody diluted to 2 μg/mL with a blocking buffer was then added thereto at 70 μL/well. One hour later, the antibody was removed, and each well was washed three times by the addition of TBS-T at 200 μL/well. An HRP-bound anti-mouse antibody was added at 70 μL/well to each well and reacted therewith for 1 hour. After removal of the antibody, each well was washed with 200 μL/well of TBS-T three times, and a chromogenic reagent ABTS Peroxidase Substrate System (1 component, KPL, Kirkegaard & Perry Laboratories, Inc.) was then added thereto at 70 μL/well and reacted at room temperature for 15 to 30 to develop color. The reaction was terminated by the addition of 1% SDS at 70 μL/well, and the absorbance at 405 nm was measured using a plate reader. As a result, as shown in FIG. 3, GT30 was found to bind to the peptide of SEQ ID NO: 17, whereas the specific binding of GT114, GT165, and GT607 was not found for these peptides.

These results suggest that GT30 binds to a site from position 321 to position 350 of GPC3 and also suggest the possibility that GT165 as well as GT114 and GT607 recognize conformation.

TABLE 2

| Amino acid position | Sequence | SEQ ID NO |
|---|---|---|
| 1-30 | MAGTVRTACLVVAMLLSLDFPGQAQPPPPP | 1 |
| 21-50 | PGQAQPPPPPPDATCHQVRSFFQRLQPGLK | 2 |
| 41-70 | FFQRLQPGLKWVPETPVPGSDLQVCLPKGP | 3 |
| 61-90 | DLQVCLPKGPTCCSRKMEEKYQLTARLNME | 4 |
| 81-110 | YQLTARLNMEQLLQSASMELKFLIIQNAAV | 5 |
| 101-130 | KFLIIQNAAVFQEAFEIVVRHAKNYTNAMF | 6 |
| 121-150 | HAKNYTNAMFKNNYPSLTPQAFEFVGEFFT | 7 |
| 141-170 | AFEFVGEFFTDVSLYILGSDINVDDMVNEL | 8 |
| 161-190 | INVDDMVNELFDSLFPVIYTQLMNPGLPDS | 9 |
| 181-210 | QLMNPGLPDSALDINECLRGARRDLKVFGN | 10 |
| 201-230 | ARRDLKVEGNFPKLIMTQVSKSLQVTRIFL | 11 |
| 221-250 | KSLQVTRIFLQALNLGIEVINTTDHLKFSK | 12 |
| 241-270 | NTTDHLKFSKDCGRMLTRMWYCSYCQGLMM | 13 |
| 261-290 | YCSYCQGLMMVKPCGGYCNVVMQGCMAGVV | 14 |
| 281-310 | VMQGCMAGVVEIDKYWREYILSLEELVNGM | 15 |

TABLE 2-continued

| Amino acid position | Sequence | SEQ ID NO |
|---|---|---|
| 301-330 | LSLEELVNGMYRIYDMENVLLGLFSTIHDS | 16 |
| 321-350 | LGLFSTIHDSIQYVQKNAGKLITTIGKLCA | 17 |
| 341-370 | LTTTIGKLCAHSQQRQYR^SAYYPEDLFIDK | 18 |
| 361-390 | YYPEDLFIDKKVLKVAHVEHEETLSSRRRE | 19 |
| 381-410 | EETLSSRRRELIQKLKSFISFYSALPGYIC | 20 |
| 401-430 | FYSALPGYICSHSPVAENDTLCWNGQELVE | 21 |
| 421-450 | LCWNGQELVERYSQKAARNGMKNQFNLHEL | 22 |

TABLE 2-continued

| Amino acid position | Sequence | SEQ ID NO |
|---|---|---|
| 441-470 | MKNQFNLHELKMKGPEPVVSQIIDKLKHIN | 23 |
| 461-490 | QIIDKLKHINQLLRTMSMPKGRVLDKNLDE | 24 |
| 481-510 | GRVLDKNLDEEGFESGDCGDDEDECIGGSG | 25 |
| 501-530 | DEDECIGGSGDGMIKVKNQLRFLAELAYDL | 26 |
| 521-550 | RFLAELAYDLDVDDAPGNSQQATPKDNEIS | 27 |
| 541-570 | QATPKDNEISTFHNLGNVHSPLKLLTSMAI | 28 |
| 551-580 | TFHNLGNVHSPLKLLTSMAISVVCFFFLVH | 29 |

Example 4

Next, in order to analyze the binding competition of each antibody recognizing the GPC3 N-terminal fragment, each antibody was used in a binding competition test.

Specifically, a 1 µg/mL sGPC3 solution (in PBS) was added at 50 µL/well to a 96-well transparent microplate (MaxiSoap manufactured by Thermo Fisher Scientific Inc.), and the microplate was left standing overnight at room temperature. Subsequently, the microplate was washed with a washing solution (TBS containing 0.01% Triton X-100) once. Then, a blocking solution (Blocking-One manufactured by Nacalai Tesque, Inc.) was added thereto at 200 µL/well, and the microplate was left standing at room temperature for 1 hour. The microplate was washed with a washing solution three times. Then, a 50 µg/mL unlabeled anti-GPC3 antibody solution (in PBS containing 20% Blocking-One) was added thereto at 25 µL/well, and the mixture was stirred at room temperature for 1 minute. A 0.5 µg/mL biotin-labeled anti-GPC3 antibody solution (in PBS containing 20% Blocking-One) was further added thereto at 25 µL/well, and the mixture was stirred at room temperature for 1 hour. Subsequently, the microplate was washed with a washing solution three times. Then, a solution of StreptAvidin-HRP (manufactured by Prozyme) diluted 10,000-fold with a diluting solution (TBS containing 10% Block Ace and 0.1% Tween 20) was added thereto at 50 µL/well, and the mixture was stirred at room temperature for 30 minutes. The microplate was washed with a washing solution five times. Then, a chromogenic substrate solution (1-Step Turbo TMB manufactured by Thermo Fisher Scientific Inc.) was added thereto at 50 µL/well, and the absorbance at 450 nm (O.D. 450) was measured using a microplate reader.

TABLE 3

| | | Labeled antibody | | | |
|---|---|---|---|---|---|
| | | GT30 | GT114 | GT607 | GT165 |
| O.D. 450 | — | 1.840 | 2.299 | 2.181 | 1.678 |
| Unlabeled antibody (added in 100-fold amount) | GT30 | 0.070 | 2.315 | 2.125 | 0.098 |
| | GT114 | 2.140 | 0.251 | 0.307 | 1.818 |
| | GT607 | 2.064 | 1.132 | 0.135 | 0.129 |
| | GT165 | 0.846 | 2.280 | 1.248 | 0.111 |
| Inhibitory effect (%) | GT30 | 96% | 0%> | 3% | 94% |
| Unlabeled antibody (added in 100-fold amount) | GT114 | 0%> | 89% | 86% | 0%> |
| | GT607 | 0%> | 51% | 94% | 92% |
| | GT165 | 54% | 1% | 43% | 93% |

Figure 4:
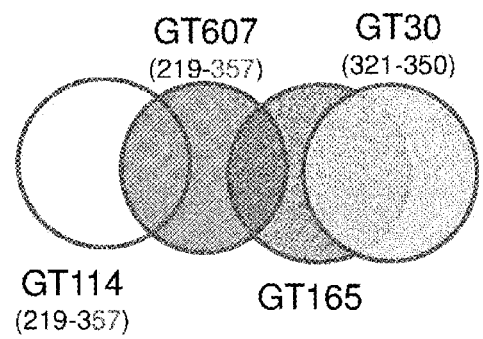
FIG. 4 schematically shows a GT30, GT114, GT607, or GT165 antibody-binding region on GPC3.
Figure 5:
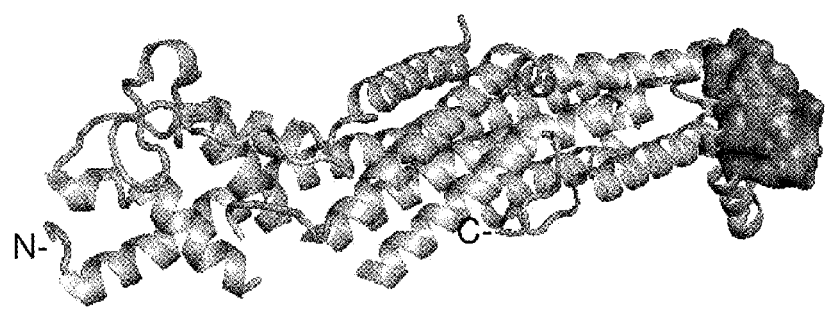
FIG. 5 shows a GT30-binding region in the conformation of human GPC3.
Figure 6:
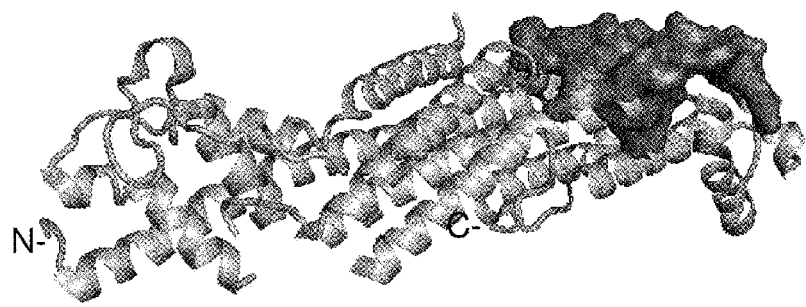
FIG. 6 shows a GT165-binding region in the conformation of human GPC3.
Figure 7:
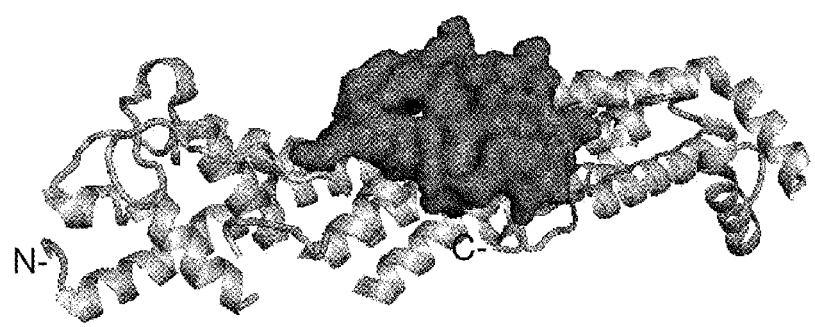
FIG. 7 shows a GT607-binding region in the conformation of human GPC3.
Figure 8:
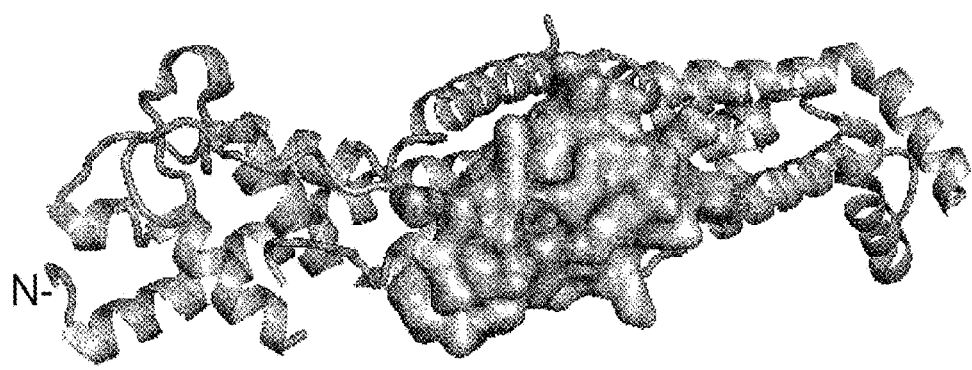
FIG. 8 shows a GT114-binding region in the conformation of human GPC3.
Figure 9:
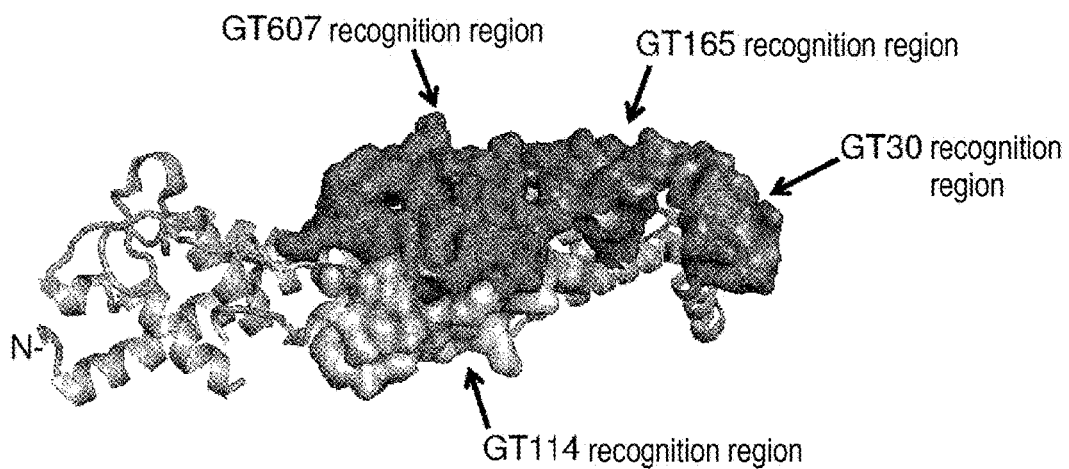
FIG. 9 shows the GT30-, GT165-, GT607- and GT114-binding regions overlaid on each other in the conformation of human GPC3.

As shown in Table 3, GT30 and GT165 mutually inhibited their binding to GPC3. Therefore, the epitopes for GT165 and GT30 seem to be located in proximity. Although GT114 and GT607 were free from inhibition by GT30, their binding to GPC3 was inhibited in the coexistence of GT114 and GT607. Therefore, the epitopes for GT114 and GT607 seem to be located in proximity. On the other hand, GT114 was also free from inhibition by GT165, whereas GT607 underwent the inhibition of binding by GT165. Therefore, the binding site of GT607 was found to not overlap with the binding site of GT30, but to be located near the binding region of GT165 (FIG. 4).

Example 5

The results described above suggested that GT114, GT165, and GT607 recognize conformation, and, particularly, GT165 binds to near the site from position 321 to position 350, which is an epitope region for GT30. Therefore, a possible binding region was identified using a conformational model of human GPC3.

First, on the hypothesis that the structure of fruit fly Dally-like protein (PDB ID: 3ODN; Kim M. S. et al., Proc Natl Acad Sci USA 2011; 108: 13112-13117) having high homology to human GPC3 and having reported results of X-ray crystallography would be the conformation of human GPC3 (containing a proline residue at position 29 to a lysine residue at position 486 except for tyrosine at position 357 to valine at position 372), the interaction of each antibody was predicted using PyMOL Molecular Graphics System, Version 1.5.0.4 (manufactured by Schrodinger LLC). The conformation of the glypican molecule has been reported to be well conserved across species (Svensson G. et al., J Biol Chem 2012; 287: 14040-14051).

As a result, the epitope region for GT30 from position 321 to position 350 was presumed to have an α-helix structure. In order to analyze a binding mode for this region, three mouse monoclonal antibody Fabs (PDB IDs: 2CMR, 2XRA, and 3V6Z) found to recognize an α-helix structure and having reported results of X-ray crystallography were used as helix structure recognition models. The X-ray crystal structure of a mouse IgG1 antibody (PDB ID: 1IGY) was further overlaid with each of these three Fabs. As a result, a total of 12 possible binding modes including all combinations of two types of helix-binding sites for the region from position 321 to position 350, the binding modes of 3 types of Fabs (2CMR, 2XRA, and 3V6Z), and two mouse IgG1 Fabs were predicted for mouse IgG1 antibodies recognizing two helix moieties in the region from position 321 to position 350 of human GPC3.

For each of these 12 IgG1 binding models, a region on human GPC3 that came in contact with Fab within 4 angstroms was identified as a binding region for GT165, which is an antibody competing with GT30 for antigen binding. Likewise, a region capable of competing with the binding region for GT165 was identified as a binding region for GT607. Subsequently, on the basis of the binding region for GT607, a region capable of competing therewith was identified as a binding region for GT114. From these results, the results of Examples 2 and 3, and the results about competitive relationships shown in Table 3 and FIG. 4, regions shown in FIGS. 5 to 9 were identified as binding regions for GT30, GT165, GT607, and GT114. Of these recognition regions identified here, human GPC3 amino acid residues that are important for the antigen binding of each antibody are described in Table 4, in light of the results of Examples 2 and 3. All human GPC3 amino acid residues that may serve as recognition regions of each antibody predicted from the structural models are shown in Table 5.

TABLE 4

| GT30 | GT165 | GT607 | GT114 |
|---|---|---|---|
| N337 | A128 | G322 | S220 |
| G339 | M129 | S325 | K221 |
| K340 | K131 | T326 | K221 |
| L341 | N132 | H328 | I228 |
| T343 | N133 | D329 | Q231 |
| T344 | Y134 | S330 | A232 |
| G346 | P135 | Q332 | L235 |
| K347 | F171 | Y333 | E291 |
| L348 | F208 | Q335 | K294 |
| C349 | G209 | K336 | Y295 |
| A350 | N210 | N337 | E298 |
|  | F211 | A338 | L301 |
|  | P212 | G339 | S302 |
|  | L214 | K340 | E305 |
|  | I215 | T344 | N308 |
|  | Q218 |  | G309 |
|  | N318 |  |  |

GT607 column continued: R297, E298, T300, L301, S302, E304, E305, L306, N308, G309, Y311, R312, T313, Y314, D315, N318

TABLE 5

| Human GPC3 amino acid position | Human GPC3 amino acid residue |
|---|---|
| 129 | Met |
| 133 | Asn |
| 134 | Tyr |
| 182 | Leu |
| 186 | Gly |
| 194 | Ile |
| 205 | Leu |
| 208 | Phe |

TABLE 5-continued

| Human GPC3 amino acid position | Human GPC3 amino acid residue |
|---|---|
| 209 | Gly |
| 210 | Asn |
| 211 | Phe |
| 214 | Leu |
| 215 | Ile |
| 218 | Gln |
| 318 | Asn |
| 351 | His |

Example 6

(Construction of ELISA Assay System Using Magnetic Particle)

On the basis of the results of Example 4, two types shown in Table 6 were selected as combinations of antibodies capable of constructing soluble GPC3 assay systems.

TABLE 6

| Assay system No. | On solid-phase side | On label side |
|---|---|---|
| 1 | GT114 | GT165 |
| 2 | GT30 | GT607 |

For each assay system shown in Table 6, the antibody on a slid-phase side was immobilized on a magnetic particle (Magnosphere MS300/Carboxyl manufactured by JSR Life Sciences Corp.), while the antibody on a label side was labeled with alkaline phosphatase in order to achieve high sensitivity.

Example 7

(Assay of Soluble GPC3 by Chemiluminescent Enzyme Immunoassay Using Magnetic Particle)

The soluble GPC3 was assayed by chemiluminescent enzyme immunoassay using magnetic particles according to the following method:

0.06% (w/v) GT30 or GT114 antibody-bound magnetic particles were added at 25 μL/wee to a 96-well white microplate (manufactured by Corning Inc.). Subsequently, a solution sample containing soluble GPC3 was added thereto at 25 μL/well. Each solution of the GT607 or GT165 antibody labeled with alkaline phosphatase was further added thereto at 25 μL/well. Then, the 96-well white microplate was stirred at 25° C. for 20 minutes. The antibody-bound magnetic particles were washed with a washing solution (TBS containing 0.01% Triton X-100) five times while magnetism was collected with a microplate washer (HydroFlex manufactured by Tecan Trading AG). A luminescent substrate solution (Lumipulse substrate solution manufactured by FUJIREBIO Inc.) was further added thereto at 50 μL/well. Five minutes later, the luminescence intensity was measured using a chemiluminescence detector (GloMax 96 manufactured by Promega Corp.).

Example 8

(Detection Limit and Quantification Limit)

For the detection limit, soluble GPC3 solution samples prepared at 0 to 10 pg/mL were each assayed 10 times. A mean and standard deviation (SD) of the luminescence intensity values measured at each concentration were calculated. Then, the lowest concentration at which the range of the mean measured luminescence intensity value±3SD did not overlap with the range of the mean measured luminescence intensity at the concentration 0 pg/mL±3SD was defined as the detection limit.

For the quantification limit, soluble GPC3 solution samples prepared at 0 to 10 pg/mL were each assayed 10 times. The concentration at which CV of the measurement values calculated from a calibration curve was 10% or less was defined as the quantification limit.

Figure 10:
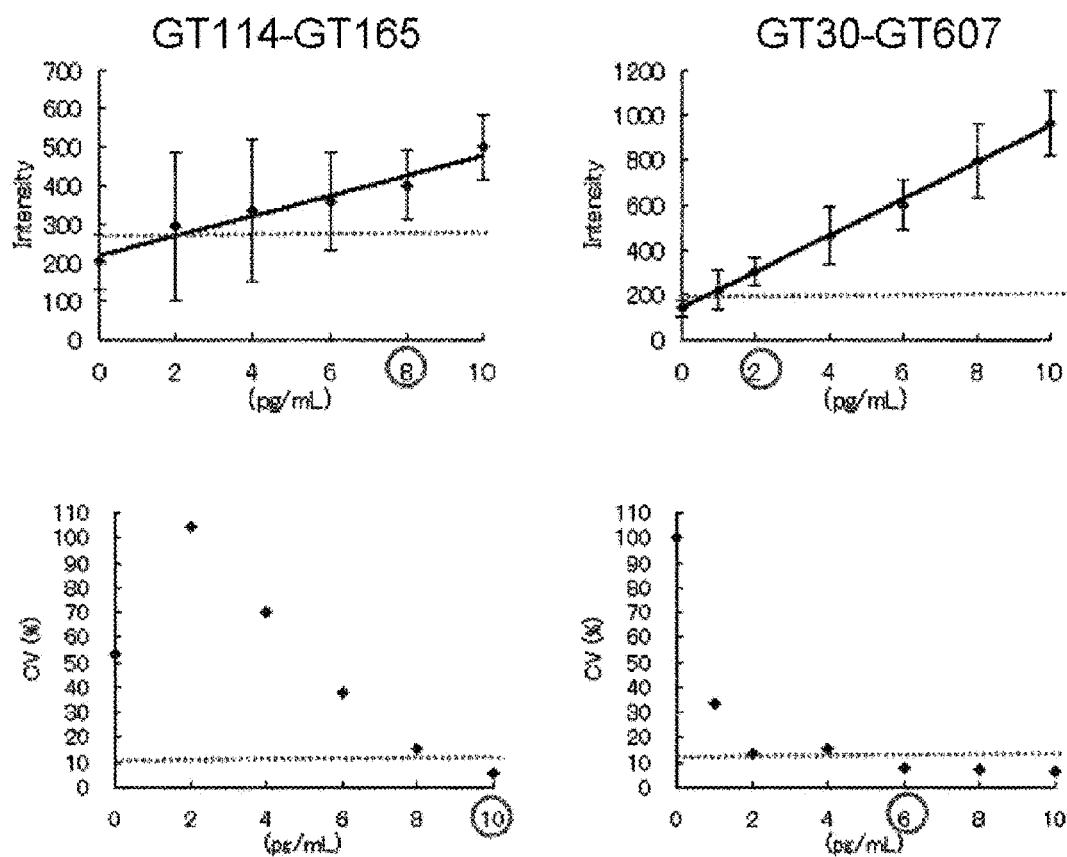
FIG. 10 is a graph showing the detection limit and the quantification limit of each assay system.

As a result, as shown in FIG. 10, all of the constructed assay systems had a detection limit and a quantification limit of 10 pg/mL or lower and were confirmed to be capable of assaying soluble GPC3 highly sensitively.

Example 9

(Dilution Linearity Test of Liver Cancer Specimen)

A calibration curve was prepared from soluble GPC3 solutions each prepared at 0, 10, 25, 50, 100, 250, 500, or 1000 pg/mL. Soluble GPC3 in serially diluted liver cancer specimens was assayed by the same procedures as in Example 7.

As a result, as shown in Table 7, values were calculated by multiplying each measurement value by each dilution ratio and evaluated for dilution linearity. Consequently, the dilution linearity was confirmed.

TABLE 7

| | Dilution ratio | GT114-GT165 | GT30-GT607 |
|---|---|---|---|
| Mean measurement value (pg/mL) | 1 | 773 | 763 |
| | 2 | 395 | 370 |
| | 4 | 192 | 181 |
| | 8 | 121 | 92 |
| | 16 | 52 | 53 |
| Measurement value × dilution ratio (pg/mL) | 1 | 773 | 763 |
| | 2 | 790 | 740 |
| | 4 | 768 | 724 |
| | 8 | 968 | 736 |
| | 16 | 832 | 848 |
| Linearity evaluation (%) | 1 | 100 | 100 |
| | 2 | 102 | 97 |
| | 4 | 99 | 95 |
| | 8 | 125 | 96 |
| | 16 | 108 | 111 |

Example 10

(Assay Using Healthy Subjects' Specimens)

A calibration curve was prepared from soluble GPC3 solutions each prepared at 0, 10, 25, 50, 100, 250, 500, or 1000 pg/mL. Soluble GPC3 in healthy subject sera was assayed by the same procedures as in Example 7. 21 healthy subjects' sera were used in the assay, and a mean of the measurement values was determined.

TABLE 8

| | | GT114-GT165 | GT30-GT607 |
|---|---|---|---|
| Measurement value (pg/mL) | Normal human 1 | 32 | 103 |
| | Normal human 2 | 53 | 99 |
| | Normal human 3 | 32 | 107 |
| | Normal human 4 | 15 | 109 |
| | Normal human 5 | 35 | 171 |
| | Normal human 6 | 21 | 129 |
| | Normal human 7 | 55 | 119 |

TABLE 8-continued

| | GT114-GT165 | GT30-GT607 |
|---|---|---|
| Normal human 8 | 20 | 138 |
| Normal human 9 | 58 | 174 |
| Normal human 10 | 25 | 86 |
| Normal human 11 | 21 | 66 |
| Normal human 12 | 41 | 125 |
| Normal human 13 | 64 | 165 |
| Normal human 14 | 55 | 122 |
| Normal human 15 | 16 | 47 |
| Normal human 16 | 17 | 128 |
| Normal human 17 | 73 | 142 |
| Normal human 18 | 52 | 127 |
| Normal human 19 | 16 | 88 |
| Normal human 20 | 51 | 116 |
| Normal human 21 | 31 | 104 |
| Mean | 37 | 117 |

As a result, as shown in Table 8, all of the measurement values of the soluble GPC3 in the healthy subjects' sera were above the detection limit and the quantification limit of each assay system, and the concentration range of the soluble GPC3 was 15 to 174 pg/mL. From these results, all of the constructed assay systems were confirmed to be capable of detecting soluble GPC3 contained at as trace as several tens to several hundreds of pg/mL in healthy subject serum.

Example 11

Sequence Analysis of Obtained Antibody

Total RNA was extracted from each of the hybridomas producing the antibodies GT30, GT114, GT165, GT607, and GT30 obtained as described above, and cDNA was synthesized therefrom using reverse transcriptase. Then, the mouse antibody genes were amplified by PCR, and nucleotide sequences each encoding the amino terminus to the variable region were determined (SEQ ID NOs: 30 to 37). The amino acid sequences of the variable regions are shown in SEQ ID NOs: 38 to 45. The sequences of their CDR regions are shown in SEQ ID NOs: 46 to 69.

Example 12

In order to confirm the efficacy and safety of GC33 in advanced and/or recurrent hepatocellular carcinoma (HCC) patients, a multicenter, randomized, double-blind, placebo-controlled phase-II clinical trial involving administering 1600 mg of GC33 every other week was conducted targeting previously treated human adult patients with unresectable advanced or metastatic hepatocellular carcinoma (NP27884 study). GC33 is a genetically recombinant humanized IgG1 monoclonal antibody binding to human GPC3 with high affinity (WO2006/006693).

The concentration of soluble GPC3 in serum before the first dose for the cases given GC33 or a placebo in the GPC3-targeting treatment was confirmed to be able to be assayed with a combination of two different antibodies binding to soluble GPC3 (combination of the GT30 antibody and the GT607 antibody or a combination of GT114 and GT165).

An antibody-bound particle solution containing GT30 or GT114 bound with magnetic particles (MS300 manufactured by JSR Life Sciences Corp.) was added at 25 μL/well to a 96-well microplate. Subsequently, a standard sample solution for a calibration curve or an appropriately diluted serum sample was added thereto at 25 μL/well, and alkaline phosphatase-labeled GT607 or GT165 was further added thereto at 25 μL/well. After shaking at 25° C. for 20 minutes, each well was washed with a washing solution five times with magnetism collected using Dyna-Mag-96 Side Skirted (manufactured by VERITAS Corp.). A luminescent substrate solution preheated to 37° C. was added thereto at 50 μL/well. The plate was shaken at room temperature for 1 minute and then left standing for 4 minutes to develop light. The chemiluminescence intensity was measured using a luminometer (manufactured by VERITAS Corp.). The GPC3 standard used in the standard sample solution for a calibration curve was recombinant GPC3 with serine residues at positions 495 and 509 substituted by alanine residues so as to prevent the binding of a heparan sulfate sugar chain (Hippo et al., Cancer Res. (2004) 64, 2418-2423).

The calibration curve (standard curve) prepared on the basis of standard samples containing the recombinant GPC3 was used to calculate the GPC3 antigen in the serum of each patient from the obtained chemiluminescence intensity of each well.

INDUSTRIAL APPLICABILITY

The present invention is useful for early detection at an initial stage in development, selection of an anticancer agent used, and post-treatment prognosis for cancer, particularly, liver cancer.

The invention claimed is:

1. An immunoassay method for assaying soluble Glypican-3 (GPC3) protein in a test sample, comprising contacting the sample with a first and a second antibody that each specifically bind to different epitopes of soluble GPC3 protein to form a complex; and detecting the complex to assay soluble GPC3 in the sample,
   wherein the first antibody comprises a heavy chain variable region comprising the amino acid sequence of SEQ ID NO: 38 and a light chain variable region comprising the amino acid sequence of SEQ ID NO: 39,
   and wherein the second antibody comprises a heavy chain variable region comprising the amino acid sequence of SEQ ID NO: 40 and a light chain variable region comprising the amino acid sequence of SEQ ID NO: 41,
   and wherein the soluble GPC3 protein comprises amino acids 128-357 of SEQ ID NO: 70.

2. The method according to claim 1, wherein any one of the two different antibodies is bound with a magnetic particle.

3. The method according to claim 1, wherein the test sample is a whole blood sample, a plasma sample, or a serum sample isolated from a human.

4. An immunoassay method for assaying soluble Glypican-3 (GPC3) protein in a test sample, comprising contacting the sample with a first and a second antibody that each specifically bind to different epitopes of soluble GPC3 protein to form a complex; and detecting the complex to assay soluble GPC3 in the sample,
   wherein the first antibody comprises three light chain complementarity determining regions (CDRs) in which CDR1 comprises the amino acid sequence of SEQ ID NO: 49, CDR2 comprises the amino acid sequence of SEQ ID NO: 50 and CDR3 comprises the amino acid sequence of SEQ ID NO: 51, and said first antibody further comprises three heavy chain complementarity determining regions (CDRs) in which CDR1 comprises the amino acid sequence of SEQ ID NO: 46, CDR2 comprises the amino acid sequence of SEQ ID NO: 47 and CDR3 comprises the amino acid sequence of SEQ ID NO: 48, and
   wherein the second antibody comprises three light chain complementarity determining regions (CDRs) in which CDR1 comprises the amino acid sequence of SEQ ID NO: 55, CDR2 comprises the amino acid sequence of SEQ ID NO: 56 and CDR3 comprises the amino acid sequence of SEQ ID NO: 57, and said second antibody further comprises three heavy chain complementarity determining regions (CDRs) in which CDR1 comprises the amino acid sequence of SEQ ID NO: 52, CDR2 comprises the amino acid sequence of SEQ ID NO: 53 and CDR3 comprises the amino acid sequence of SEQ ID NO: 54, and wherein the soluble GPC3 protein comprises amino acids 128-357 of SEQ ID NO: 70.

5. The method according to claim 4, wherein any one of the two different antibodies is bound with a magnetic particle.

6. The method according to claim 4, wherein the test sample is a whole blood sample, a plasma sample, or a serum sample isolated from a human.

* * * * *

SEQUENCE LISTING

```
<160> NUMBER OF SEQ ID NOS: 70

<210> SEQ ID NO 1
<211> LENGTH: 30
<212> TYPE: PRT
<213> ORGANISM: Mus musculus

<400> SEQUENCE: 1

Met Ala Gly Thr Val Arg Thr Ala Cys Leu Val Val Ala Met Leu Leu
1               5                   10                  15

Ser Leu Asp Phe Pro Gly Gln Ala Gln Pro Pro Pro Pro
            20                  25                  30

<210> SEQ ID NO 2
<211> LENGTH: 30
<212> TYPE: PRT
<213> ORGANISM: Mus musculus

<400> SEQUENCE: 2

Pro Gly Gln Ala Gln Pro Pro Pro Pro Pro Asp Ala Thr Cys His
1               5                   10                  15

Gln Val Arg Ser Phe Phe Gln Arg Leu Gln Pro Gly Leu Lys
            20                  25                  30

<210> SEQ ID NO 3
<211> LENGTH: 30
<212> TYPE: PRT
<213> ORGANISM: Mus musculus

<400> SEQUENCE: 3

Phe Phe Gln Arg Leu Gln Pro Gly Leu Lys Trp Val Pro Glu Thr Pro
1               5                   10                  15

Val Pro Gly Ser Asp Leu Gln Val Cys Leu Pro Lys Gly Pro
            20                  25                  30

<210> SEQ ID NO 4
<211> LENGTH: 30
<212> TYPE: PRT
<213> ORGANISM: Mus musculus

<400> SEQUENCE: 4

Asp Leu Gln Val Cys Leu Pro Lys Gly Pro Thr Cys Cys Ser Arg Lys
1               5                   10                  15

Met Glu Glu Lys Tyr Gln Leu Thr Ala Arg Leu Asn Met Glu
            20                  25                  30

<210> SEQ ID NO 5
<211> LENGTH: 30
<212> TYPE: PRT
```

<213> ORGANISM: Mus musculus

<400> SEQUENCE: 5

Tyr Gln Leu Thr Ala Arg Leu Asn Met Glu Gln Leu Gln Ser Ala
1               5                   10                  15
Ser Met Glu Leu Lys Phe Leu Ile Ile Gln Asn Ala Ala Val
            20                  25                  30

<210> SEQ ID NO 6
<211> LENGTH: 30
<212> TYPE: PRT
<213> ORGANISM: Mus musculus

<400> SEQUENCE: 6

Lys Phe Leu Ile Ile Gln Asn Ala Ala Val Phe Gln Glu Ala Phe Glu
1               5                   10                  15
Ile Val Val Arg His Ala Lys Asn Tyr Thr Asn Ala Met Phe
            20                  25                  30

<210> SEQ ID NO 7
<211> LENGTH: 30
<212> TYPE: PRT
<213> ORGANISM: Mus musculus

<400> SEQUENCE: 7

His Ala Lys Asn Tyr Thr Asn Ala Met Phe Lys Asn Asn Tyr Pro Ser
1               5                   10                  15
Leu Thr Pro Gln Ala Phe Glu Phe Val Gly Glu Phe Phe Thr
            20                  25                  30

<210> SEQ ID NO 8
<211> LENGTH: 30
<212> TYPE: PRT
<213> ORGANISM: Mus musculus

<400> SEQUENCE: 8

Ala Phe Glu Phe Val Gly Glu Phe Phe Thr Asp Val Ser Leu Tyr Ile
1               5                   10                  15
Leu Gly Ser Asp Ile Asn Val Asp Met Val Asn Glu Leu
            20                  25                  30

<210> SEQ ID NO 9
<211> LENGTH: 30
<212> TYPE: PRT
<213> ORGANISM: Mus musculus

<400> SEQUENCE: 9

Ile Asn Val Asp Asp Met Val Asn Glu Leu Phe Asp Ser Leu Phe Pro
1               5                   10                  15
Val Ile Tyr Thr Gln Leu Met Asn Pro Gly Leu Pro Asp Ser
            20                  25                  30

<210> SEQ ID NO 10
<211> LENGTH: 30
<212> TYPE: PRT
<213> ORGANISM: Mus musculus

<400> SEQUENCE: 10

Gln Leu Met Asn Pro Gly Leu Pro Asp Ser Ala Leu Asp Ile Asn Glu
1               5                   10                  15
Cys Leu Arg Gly Ala Arg Arg Asp Leu Lys Val Phe Gly Asn
            20                  25                  30

<210> SEQ ID NO 11
<211> LENGTH: 30
<212> TYPE: PRT
<213> ORGANISM: Mus musculus

<400> SEQUENCE: 11

Ala Arg Arg Asp Leu Lys Val Phe Gly Asn Phe Pro Lys Leu Ile Met
1               5                   10                  15

Thr Gln Val Ser Lys Ser Leu Gln Val Thr Arg Ile Phe Leu
            20                  25                  30

<210> SEQ ID NO 12
<211> LENGTH: 30
<212> TYPE: PRT
<213> ORGANISM: Mus musculus

<400> SEQUENCE: 12

Lys Ser Leu Gln Val Thr Arg Ile Phe Leu Gln Ala Leu Asn Leu Gly
1               5                   10                  15

Ile Glu Val Ile Asn Thr Thr Asp His Leu Lys Phe Ser Lys
            20                  25                  30

<210> SEQ ID NO 13
<211> LENGTH: 30
<212> TYPE: PRT
<213> ORGANISM: Mus musculus

<400> SEQUENCE: 13

Asn Thr Thr Asp His Leu Lys Phe Ser Lys Asp Cys Gly Arg Met Leu
1               5                   10                  15

Thr Arg Met Trp Tyr Cys Ser Tyr Cys Gln Gly Leu Met Met
            20                  25                  30

<210> SEQ ID NO 14
<211> LENGTH: 30
<212> TYPE: PRT
<213> ORGANISM: Mus musculus

<400> SEQUENCE: 14

Tyr Cys Ser Tyr Cys Gln Gly Leu Met Met Val Lys Pro Cys Gly Gly
1               5                   10                  15

Tyr Cys Asn Val Val Met Gln Gly Cys Met Ala Gly Val Val
            20                  25                  30

<210> SEQ ID NO 15
<211> LENGTH: 30
<212> TYPE: PRT
<213> ORGANISM: Mus musculus

<400> SEQUENCE: 15

Val Met Gln Gly Cys Met Ala Gly Val Val Glu Ile Asp Lys Tyr Trp
1               5                   10                  15

Arg Glu Tyr Ile Leu Ser Leu Glu Glu Leu Val Asn Gly Met
            20                  25                  30

<210> SEQ ID NO 16
<211> LENGTH: 30
<212> TYPE: PRT
<213> ORGANISM: Mus musculus

<400> SEQUENCE: 16

```
Leu Ser Leu Glu Glu Leu Val Asn Gly Met Tyr Arg Ile Tyr Asp Met
1               5                   10                  15

Glu Asn Val Leu Leu Gly Leu Phe Ser Thr Ile His Asp Ser
            20                  25                  30

<210> SEQ ID NO 17
<211> LENGTH: 30
<212> TYPE: PRT
<213> ORGANISM: Mus musculus

<400> SEQUENCE: 17

Leu Gly Leu Phe Ser Thr Ile His Asp Ser Ile Gln Tyr Val Gln Lys
1               5                   10                  15

Asn Ala Gly Lys Leu Thr Thr Thr Ile Gly Lys Leu Cys Ala
            20                  25                  30

<210> SEQ ID NO 18
<211> LENGTH: 30
<212> TYPE: PRT
<213> ORGANISM: Mus musculus

<400> SEQUENCE: 18

Leu Thr Thr Thr Ile Gly Lys Leu Cys Ala His Ser Gln Gln Arg Gln
1               5                   10                  15

Tyr Arg Ser Ala Tyr Tyr Pro Glu Asp Leu Phe Ile Asp Lys
            20                  25                  30

<210> SEQ ID NO 19
<211> LENGTH: 30
<212> TYPE: PRT
<213> ORGANISM: Mus musculus

<400> SEQUENCE: 19

Tyr Tyr Pro Glu Asp Leu Phe Ile Asp Lys Lys Val Leu Lys Val Ala
1               5                   10                  15

His Val Glu His Glu Thr Leu Ser Ser Arg Arg Glu
            20                  25                  30

<210> SEQ ID NO 20
<211> LENGTH: 30
<212> TYPE: PRT
<213> ORGANISM: Mus musculus

<400> SEQUENCE: 20

Glu Glu Thr Leu Ser Ser Arg Arg Arg Glu Leu Ile Gln Lys Leu Lys
1               5                   10                  15

Ser Phe Ile Ser Phe Tyr Ser Ala Leu Pro Gly Tyr Ile Cys
            20                  25                  30

<210> SEQ ID NO 21
<211> LENGTH: 30
<212> TYPE: PRT
<213> ORGANISM: Mus musculus

<400> SEQUENCE: 21

Phe Tyr Ser Ala Leu Pro Gly Tyr Ile Cys Ser His Ser Pro Val Ala
1               5                   10                  15

Glu Asn Asp Thr Leu Cys Trp Asn Gly Gln Glu Leu Val Glu
            20                  25                  30

<210> SEQ ID NO 22
<211> LENGTH: 30
```

```
<212> TYPE: PRT
<213> ORGANISM: Mus musculus

<400> SEQUENCE: 22

Leu Cys Trp Asn Gly Gln Glu Leu Val Glu Arg Tyr Ser Gln Lys Ala
1               5                   10                  15

Ala Arg Asn Gly Met Lys Asn Gln Phe Asn Leu His Glu Leu
            20                  25                  30

<210> SEQ ID NO 23
<211> LENGTH: 30
<212> TYPE: PRT
<213> ORGANISM: Mus musculus

<400> SEQUENCE: 23

Met Lys Asn Gln Phe Asn Leu His Glu Leu Lys Met Lys Gly Pro Glu
1               5                   10                  15

Pro Val Val Ser Gln Ile Ile Asp Lys Leu Lys His Ile Asn
            20                  25                  30

<210> SEQ ID NO 24
<211> LENGTH: 30
<212> TYPE: PRT
<213> ORGANISM: Mus musculus

<400> SEQUENCE: 24

Gln Ile Ile Asp Lys Leu Lys His Ile Asn Gln Leu Leu Arg Thr Met
1               5                   10                  15

Ser Met Pro Lys Gly Arg Val Leu Asp Lys Asn Leu Asp Glu
            20                  25                  30

<210> SEQ ID NO 25
<211> LENGTH: 30
<212> TYPE: PRT
<213> ORGANISM: Mus musculus

<400> SEQUENCE: 25

Gly Arg Val Leu Asp Lys Asn Leu Asp Glu Glu Gly Phe Glu Ser Gly
1               5                   10                  15

Asp Cys Gly Asp Asp Glu Asp Glu Cys Ile Gly Gly Ser Gly
            20                  25                  30

<210> SEQ ID NO 26
<211> LENGTH: 30
<212> TYPE: PRT
<213> ORGANISM: Mus musculus

<400> SEQUENCE: 26

Asp Glu Asp Glu Cys Ile Gly Gly Ser Gly Asp Gly Met Ile Lys Val
1               5                   10                  15

Lys Asn Gln Leu Arg Phe Leu Ala Glu Leu Ala Tyr Asp Leu
            20                  25                  30

<210> SEQ ID NO 27
<211> LENGTH: 30
<212> TYPE: PRT
<213> ORGANISM: Mus musculus

<400> SEQUENCE: 27

Arg Phe Leu Ala Glu Leu Ala Tyr Asp Leu Asp Val Asp Asp Ala Pro
1               5                   10                  15

Gly Asn Ser Gln Gln Ala Thr Pro Lys Asp Asn Glu Ile Ser
```

<210> SEQ ID NO 28
<211> LENGTH: 30
<212> TYPE: PRT
<213> ORGANISM: Mus musculus

<400> SEQUENCE: 28

Gln Ala Thr Pro Lys Asp Asn Glu Ile Ser Thr Phe His Asn Leu Gly
1               5                   10                  15

Asn Val His Ser Pro Leu Lys Leu Leu Thr Ser Met Ala Ile
            20                  25                  30

<210> SEQ ID NO 29
<211> LENGTH: 30
<212> TYPE: PRT
<213> ORGANISM: Mus musculus

<400> SEQUENCE: 29

Thr Phe His Asn Leu Gly Asn Val His Ser Pro Leu Lys Leu Leu Thr
1               5                   10                  15

Ser Met Ala Ile Ser Val Val Cys Phe Phe Phe Leu Val His
            20                  25                  30

<210> SEQ ID NO 30
<211> LENGTH: 420
<212> TYPE: DNA
<213> ORGANISM: Mus musculus

<400> SEQUENCE: 30
atggaatgga tctggatctt tctcttcatc ctgtcaggaa ctgcaggtgt ccaatcccag      60
gttcagctgc agcagtctgg agctgagctg gcgaggcctg ggcttcagt gaaactgtcc     120
tgcagggctt ctggctacac cttcacaagc tatggtataa gctggatgat gcagagaact     180
ggacagggcc ttgagtggat tgagagatt tatcctagaa gtggtattac ttactacaat     240
gagaagttca agggcaaggc cacactgact gcagacaaat cctccagcac agcctacatg     300
cagctcagca gcctgacatc tgaggactct gcagtctatt tctgtgcaag agatgtctct     360
gatggttacc tttttcctta ctggggccaa gggactctgg tcactgtctc tgcagccaaa     420

<210> SEQ ID NO 31
<211> LENGTH: 387
<212> TYPE: DNA
<213> ORGANISM: Mus musculus

<400> SEQUENCE: 31
atgagtgtgc ccactcaggt cctggggttg ctgctgctgt ggcttacagg tgccagatgt      60
gacatccaga tgactcagtc tccagcctcc ctatctgcat ctgtgggaga aactgtcacc     120
atcacatgtc gaacaagtga gaatatttac agttatttag catggtatca gcagaaacag     180
ggaaaatctc ctcagctcct ggtctataat gcaaaaacct accagaagg tgtgccatca     240
aggttcagtg gcagtggatc aggcacacag tttttctctga agatcaacag cctgcagcct     300
gaagattttg ggagttatta ctgtcaacat cattatggta ctcctccgac gttcggtgga     360
ggcaccaagc tggaaatcaa acgggct                                         387

<210> SEQ ID NO 32
<211> LENGTH: 417
<212> TYPE: DNA
<213> ORGANISM: Mus musculus

<400> SEQUENCE: 32

```
atgaacttcg ggctcagctt gattttcctt gccctcattt taaaaggtgt ccagtgtgag      60
gtgcagctgg tggagtctgg gggagacgta gtgagacctg gagggtccct gaaactctcc     120
tgtgcagcct ctggattcac tttcagtagt tatggcatgt cctgggttcg ccagcttcca     180
gacaagaggc tggagtgggt cgcaagtgtt ggtaatggag gtagttacag gtactatcca     240
gagaatttga aggggcggtt caccatctcc agagacaata ccaagaacac cctatacctg     300
caaattagtg gtctgaagtc tgaggacaca gccatttatt actgtgcaag acggggggct     360
ttcccgtact cgatgtctg gggcgcaggg accacggtca ccgtctcctc agccaaa        417
```

<210> SEQ ID NO 33
<211> LENGTH: 390
<212> TYPE: DNA
<213> ORGANISM: Mus musculus

<400> SEQUENCE: 33

```
atggattttc aagtgcagat tttcagcttc ctgctaatca gtgcctcagt catagtatcc      60
agaggacaaa ttgttctcac ccagtctcca gcaatcatgt ctgcatctcc aggggagaag     120
gtcaccctgg cctgcagtgc cagctcaagt gtaacttaca tgcactggta ccagcagaag     180
tcaggcacct cccccaaaag atggatttat gaaacatcca actggcttc tggagtccct     240
cctcgcttca gtggcagtgg gtctgggacc tcttactctc tcacaatcag caccatggag     300
gctgaagatg ctgccactta ttactgccaa cagtggagta gtaacccgct cacgttcggt     360
gctgggacca agctggagct gaaacgggct                                       390
```

<210> SEQ ID NO 34
<211> LENGTH: 408
<212> TYPE: DNA
<213> ORGANISM: Mus musculus

<400> SEQUENCE: 34

```
atgagagtgc tgattctttt gtggctgttc acagcctttc ctggtatcct atctgatgtg      60
cagcttcagg agtcgggacc tggcctggtg aaaccttctc agtctctgtc cctcacctgc     120
actgtcactg gctactcaat caccagtgat tctgcctgga actggatccg gcagtttcca     180
ggaaacaaac tggagtggat ggcctacata atgtacagtg gatcactag ctacaatcca     240
tctctcaaaa gtcgaatctc tatcactcga gacacagcca agaaccagtt ctttctgcag     300
ttgaattctg tgactactga ggactcagcc acatattact gttcacgagg ctactggtac     360
ttcgatgtct ggggcgcagg gactacggtc accgtctcct cagccaaa                  408
```

<210> SEQ ID NO 35
<211> LENGTH: 387
<212> TYPE: DNA
<213> ORGANISM: Mus musculus

<400> SEQUENCE: 35

```
atggattttc aggtgcagat tttcagcttc ctgctaatca gtgcctcagt cataatgtcc      60
agaggacaaa ttgttctcac ccagtctcca gcaatcatgt ctgcatctct aggggaggag     120
atcaccctaa cctgcagtgc cagctcgagt gtgagttaca tgcactggta ccagcagaag     180
tcaggcactt ctcccaaact cttgatttat agcacatcca tcctggcttc tggagtccct     240
tctcgcttca gtggcagtgg gtctgggacc tttattctc tcacaatcag cagtgtggag     300
```

```
gctgaagatg ctgccgatta ttactgcctt cagtggatta cttatcggac gttcggtgga    360
ggcaccaagc tggaaatcaa acgggct                                        387
```

<210> SEQ ID NO 36
<211> LENGTH: 414
<212> TYPE: DNA
<213> ORGANISM: Mus musculus

<400> SEQUENCE: 36

```
atgtgttgga gctgtatcat cctcttcctg ttagcaacag ctgcacgtgt gcactcccag    60
gtccagctgc agcagtctgg ggctgagctg gtggggcctg ggcctcagt gaagatttcc    120 tgcaaggctt ttggctacac cttcacaaac catcatataa actgggtgaa gcagaggcct    180
ggacagggcc tggactggat tggatatatt aatccttata atgattatac taactacaac    240
cagaagttca agggcaaggc cacattgact gtagacaaat cctccagcac agcctatatg    300
gagcttagca gcctgacatc tgaggactct gcagtctatt actgtgcaag atcagacccc    360
gcctggtttg cttactgggg ccaagggact ctggtcactg tctctgcagc caaa          414
```

<210> SEQ ID NO 37
<211> LENGTH: 387
<212> TYPE: DNA
<213> ORGANISM: Mus musculus

<400> SEQUENCE: 37

```
atgagaccct ccattcagtt cctggggctc ttgttgttct ggcttcatgg tgctcagtgt    60
gacatccaga tgacacagtc tccatcctca ctgtctgcat ctctgggagg caaagtcacc    120
atcacttgca aggcaagcca agacattaac aagaatatag cttggtacca acacaagcct    180
ggaaaaggtc ctaggctgct catatggtac acatatacat tacaaccagg catcccatca    240
aggttcagtg aagtggatc tgggagagat tattccttca gcatcagcaa cctggagcct    300
gaagatattg caacttatta ctgtctacag tatgataatc ttccattcac gttcggcacg    360
gggacaaaat tggaaataaa acgggct                                        387
```

<210> SEQ ID NO 38
<211> LENGTH: 121
<212> TYPE: PRT
<213> ORGANISM: Mus musculus

<400> SEQUENCE: 38

```
Gln Val Gln Leu Gln Gln Ser Gly Ala Glu Leu Ala Arg Pro Gly Ala
  1               5                  10                  15

Ser Val Lys Leu Ser Cys Arg Ala Ser Gly Tyr Thr Phe Thr Ser Tyr
                 20                  25                  30

Gly Ile Ser Trp Met Met Gln Arg Thr Gly Gln Gly Leu Glu Trp Ile
             35                  40                  45

Gly Glu Ile Tyr Pro Arg Ser Gly Ile Thr Tyr Tyr Asn Glu Lys Phe
         50                  55                  60

Lys Gly Lys Ala Thr Leu Thr Ala Asp Lys Ser Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Arg Asp Val Ser Asp Gly Tyr Leu Phe Pro Tyr Trp Gly Gln Gly
                100                 105                 110

Thr Leu Val Thr Val Ser Ala Ala Lys
            115                 120
```

```
<210> SEQ ID NO 39
<211> LENGTH: 109
<212> TYPE: PRT
<213> ORGANISM: Mus musculus

<400> SEQUENCE: 39

Asp Ile Gln Met Thr Gln Ser Pro Ala Ser Leu Ser Ala Ser Val Gly
1               5                   10                  15

Glu Thr Val Thr Ile Thr Cys Arg Thr Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Pro Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Pro
                85                  90                  95

Thr Phe Gly Gly Gly Thr Lys Leu Glu Ile Lys Arg Ala
            100                 105

<210> SEQ ID NO 40
<211> LENGTH: 120
<212> TYPE: PRT
<213> ORGANISM: Mus musculus

<400> SEQUENCE: 40

Glu Val Gln Leu Val Glu Ser Gly Gly Asp Val Val Arg Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Leu Pro Asp Lys Arg Leu Glu Trp Val
        35                  40                  45

Ala Ser Val Gly Asn Gly Gly Ser Tyr Arg Tyr Tyr Pro Glu Asn Leu
    50                  55                  60

Lys Gly Arg Phe Thr Ile Ser Arg Asp Asn Thr Lys Asn Thr Leu Tyr
65                  70                  75                  80

Leu Gln Ile Ser Gly Leu Lys Ser Glu Asp Thr Ala Ile Tyr Tyr Cys
                85                  90                  95

Ala Arg Arg Gly Ala Phe Pro Tyr Phe Asp Val Trp Gly Ala Gly Thr
            100                 105                 110

Thr Val Thr Val Ser Ser Ala Lys
        115                 120

<210> SEQ ID NO 41
<211> LENGTH: 108
<212> TYPE: PRT
<213> ORGANISM: Mus musculus

<400> SEQUENCE: 41

Gln Ile Val Leu Thr Gln Ser Pro Ala Ile Met Ser Ala Ser Pro Gly
1               5                   10                  15

Glu Lys Val Thr Leu Ala Cys Ser Ala Ser Ser Ser Val Thr Tyr Met
            20                  25                  30

His Trp Tyr Gln Gln Lys Ser Gly Thr Ser Pro Lys Arg Trp Ile Tyr
        35                  40                  45
```

Glu Thr Ser Lys Leu Ala Ser Gly Val Pro Pro Arg Phe Ser Gly Ser
 50                  55                  60

Gly Ser Gly Thr Ser Tyr Ser Leu Thr Ile Ser Thr Met Glu Ala Glu
 65                  70                  75                  80

Asp Ala Ala Thr Tyr Tyr Cys Gln Gln Trp Ser Ser Asn Pro Leu Thr
                 85                  90                  95

Phe Gly Ala Gly Thr Lys Leu Glu Leu Lys Arg Ala
            100                 105

<210> SEQ ID NO 42
<211> LENGTH: 118
<212> TYPE: PRT
<213> ORGANISM: Mus musculus

<400> SEQUENCE: 42

Asp Val Gln Leu Gln Glu Ser Gly Pro Gly Leu Val Lys Pro Ser Gln
 1               5                   10                  15

Ser Leu Ser Leu Thr Cys Thr Val Thr Gly Tyr Ser Ile Thr Ser Asp
                 20                  25                  30

Ser Ala Trp Asn Trp Ile Arg Gln Phe Pro Gly Asn Lys Leu Glu Trp
             35                  40                  45

Met Ala Tyr Ile Met Tyr Ser Gly Ile Thr Ser Tyr Asn Pro Ser Leu
 50                  55                  60

Lys Ser Arg Ile Ser Ile Thr Arg Asp Thr Ala Lys Asn Gln Phe Phe
 65                  70                  75                  80

Leu Gln Leu Asn Ser Val Thr Thr Glu Asp Ser Ala Thr Tyr Tyr Cys
                 85                  90                  95

Ser Arg Gly Tyr Trp Tyr Phe Asp Val Trp Gly Ala Gly Thr Thr Val
            100                 105                 110

Thr Val Ser Ser Ala Lys
        115

<210> SEQ ID NO 43
<211> LENGTH: 107
<212> TYPE: PRT
<213> ORGANISM: Mus musculus

<400> SEQUENCE: 43

Gln Ile Val Leu Thr Gln Ser Pro Ala Ile Met Ser Ala Ser Leu Gly
 1               5                   10                  15

Glu Glu Ile Thr Leu Thr Cys Ser Ala Ser Ser Ser Val Ser Tyr Met
                 20                  25                  30

His Trp Tyr Gln Gln Lys Ser Gly Thr Ser Pro Lys Leu Leu Ile Tyr
             35                  40                  45

Ser Thr Ser Ile Leu Ala Ser Gly Val Pro Ser Arg Phe Ser Gly Ser
 50                  55                  60

Gly Ser Gly Thr Phe Tyr Ser Leu Thr Ile Ser Ser Val Glu Ala Glu
 65                  70                  75                  80

Asp Ala Ala Asp Tyr Tyr Cys Leu Gln Trp Ile Thr Tyr Arg Thr Phe
                 85                  90                  95

Gly Gly Gly Thr Lys Leu Glu Ile Lys Arg Ala
            100                 105

<210> SEQ ID NO 44
<211> LENGTH: 119
<212> TYPE: PRT
<213> ORGANISM: Mus musculus

<400> SEQUENCE: 44

Gln Val Gln Leu Gln Gln Ser Gly Ala Glu Leu Val Gly Pro Gly Ala
1               5                   10                  15

Ser Val Lys Ile Ser Cys Lys Ala Phe Gly Tyr Thr Phe Thr Asn His
                20                  25                  30

His Ile Asn Trp Val Lys Gln Arg Pro Gly Gln Gly Leu Asp Trp Ile
            35                  40                  45

Gly Tyr Ile Asn Pro Tyr Asn Asp Tyr Thr Tyr Asn Gln Lys Phe
        50                  55                  60

Lys Gly Lys Ala Thr Leu Thr Val Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Ser Asp Pro Ala Trp Phe Ala Tyr Trp Gly Gln Gly Thr Leu
            100                 105                 110

Val Thr Val Ser Ala Ala Lys
            115

<210> SEQ ID NO 45
<211> LENGTH: 109
<212> TYPE: PRT
<213> ORGANISM: Mus musculus

<400> SEQUENCE: 45

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Asn
                20                  25                  30

Ile Ala Trp Tyr Gln His Lys Pro Gly Lys Gly Pro Arg Leu Leu Ile
            35                  40                  45

Trp Tyr Thr Tyr Thr Leu Gln Pro Gly Ile Pro Ser Arg Phe Ser Gly
        50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asn Leu Pro Phe
                85                  90                  95

Thr Phe Gly Thr Gly Thr Lys Leu Glu Ile Lys Arg Ala
            100                 105

<210> SEQ ID NO 46
<211> LENGTH: 5
<212> TYPE: PRT
<213> ORGANISM: Mus musculus

<400> SEQUENCE: 46

Ser Tyr Gly Ile Ser
1               5

<210> SEQ ID NO 47
<211> LENGTH: 17
<212> TYPE: PRT
<213> ORGANISM: Mus musculus

<400> SEQUENCE: 47

Glu Ile Tyr Pro Arg Ser Gly Ile Thr Tyr Tyr Asn Glu Lys Phe Lys
1               5                   10                  15

Gly

```
<210> SEQ ID NO 48
<211> LENGTH: 10
<212> TYPE: PRT
<213> ORGANISM: Mus musculus

<400> SEQUENCE: 48

Asp Val Ser Asp Gly Tyr Leu Phe Pro Tyr
1               5                   10

<210> SEQ ID NO 49
<211> LENGTH: 11
<212> TYPE: PRT
<213> ORGANISM: Mus musculus

<400> SEQUENCE: 49

Arg Thr Ser Glu Asn Ile Tyr Ser Tyr Leu Ala
1               5                   10

<210> SEQ ID NO 50
<211> LENGTH: 7
<212> TYPE: PRT
<213> ORGANISM: Mus musculus

<400> SEQUENCE: 50

Asn Ala Lys Thr Leu Pro Glu
1               5

<210> SEQ ID NO 51
<211> LENGTH: 9
<212> TYPE: PRT
<213> ORGANISM: Mus musculus

<400> SEQUENCE: 51

Gln His His Tyr Gly Thr Pro Pro Thr
1               5

<210> SEQ ID NO 52
<211> LENGTH: 5
<212> TYPE: PRT
<213> ORGANISM: Mus musculus

<400> SEQUENCE: 52

Ser Tyr Gly Met Ser
1               5

<210> SEQ ID NO 53
<211> LENGTH: 17
<212> TYPE: PRT
<213> ORGANISM: Mus musculus

<400> SEQUENCE: 53

Ser Val Gly Asn Gly Gly Ser Tyr Arg Tyr Tyr Pro Glu Asn Leu Lys
1               5                   10                  15

Gly

<210> SEQ ID NO 54
<211> LENGTH: 9
<212> TYPE: PRT
<213> ORGANISM: Mus musculus

<400> SEQUENCE: 54

Arg Gly Ala Phe Pro Tyr Phe Asp Val
1               5
```

```
<210> SEQ ID NO 55
<211> LENGTH: 10
<212> TYPE: PRT
<213> ORGANISM: Mus musculus

<400> SEQUENCE: 55

Ser Ala Ser Ser Ser Val Thr Tyr Met His
1               5                   10

<210> SEQ ID NO 56
<211> LENGTH: 7
<212> TYPE: PRT
<213> ORGANISM: Mus musculus

<400> SEQUENCE: 56

Glu Thr Ser Lys Leu Ala Ser
1               5

<210> SEQ ID NO 57
<211> LENGTH: 9
<212> TYPE: PRT
<213> ORGANISM: Mus musculus

<400> SEQUENCE: 57

Gln Gln Trp Ser Ser Asn Pro Leu Thr
1               5

<210> SEQ ID NO 58
<211> LENGTH: 5
<212> TYPE: PRT
<213> ORGANISM: Mus musculus

<400> SEQUENCE: 58

Asn His His Ile Asn
1               5

<210> SEQ ID NO 59
<211> LENGTH: 17
<212> TYPE: PRT
<213> ORGANISM: Mus musculus

<400> SEQUENCE: 59

Tyr Ile Asn Pro Tyr Asn Asp Tyr Thr Asn Tyr Asn Gln Lys Phe Lys
1               5                   10                  15

Gly

<210> SEQ ID NO 60
<211> LENGTH: 8
<212> TYPE: PRT
<213> ORGANISM: Mus musculus

<400> SEQUENCE: 60

Ser Asp Pro Ala Trp Phe Ala Tyr
1               5

<210> SEQ ID NO 61
<211> LENGTH: 11
<212> TYPE: PRT
<213> ORGANISM: Mus musculus

<400> SEQUENCE: 61

Lys Ala Ser Gln Asp Ile Asn Lys Asn Ile Ala
1               5                   10
```

```
<210> SEQ ID NO 62
<211> LENGTH: 7
<212> TYPE: PRT
<213> ORGANISM: Mus musculus

<400> SEQUENCE: 62

Tyr Thr Tyr Thr Leu Gln Pro
1               5

<210> SEQ ID NO 63
<211> LENGTH: 19
<212> TYPE: PRT
<213> ORGANISM: Mus musculus

<400> SEQUENCE: 63

Leu Gln Tyr Asp Asn Leu Pro Phe Thr Phe Gly Thr Gly Thr Lys Leu
1               5                   10                  15

Glu Ile Lys

<210> SEQ ID NO 64
<211> LENGTH: 6
<212> TYPE: PRT
<213> ORGANISM: Mus musculus

<400> SEQUENCE: 64

Ser Asp Ser Ala Trp Asn
1               5

<210> SEQ ID NO 65
<211> LENGTH: 16
<212> TYPE: PRT
<213> ORGANISM: Mus musculus

<400> SEQUENCE: 65

Tyr Ile Met Tyr Ser Gly Ile Thr Ser Tyr Asn Pro Ser Leu Lys Ser
1               5                   10                  15

<210> SEQ ID NO 66
<211> LENGTH: 7
<212> TYPE: PRT
<213> ORGANISM: Mus musculus

<400> SEQUENCE: 66

Gly Tyr Trp Tyr Phe Asp Val
1               5

<210> SEQ ID NO 67
<211> LENGTH: 10
<212> TYPE: PRT
<213> ORGANISM: Mus musculus

<400> SEQUENCE: 67

Ser Ala Ser Ser Ser Val Ser Tyr Met His
1               5                   10

<210> SEQ ID NO 68
<211> LENGTH: 7
<212> TYPE: PRT
<213> ORGANISM: Mus musculus

<400> SEQUENCE: 68

Ser Thr Ser Ile Leu Ala Ser
1               5
```

<210> SEQ ID NO 69
<211> LENGTH: 8
<212> TYPE: PRT
<213> ORGANISM: Mus musculus

<400> SEQUENCE: 69

Leu Gln Trp Ile Thr Tyr Arg Thr
1               5

<210> SEQ ID NO 70
<211> LENGTH: 580
<212> TYPE: PRT
<213> ORGANISM: Homo sapiens

<400> SEQUENCE: 70

Met Ala Gly Thr Val Arg Thr Ala Cys Leu Val Val Ala Met Leu Leu
1               5                   10                  15

Ser Leu Asp Phe Pro Gly Gln Ala Gln Pro Pro Pro Pro Pro Pro Asp
            20                  25                  30

Ala Thr Cys His Gln Val Arg Ser Phe Phe Gln Arg Leu Gln Pro Gly
        35                  40                  45

Leu Lys Trp Val Pro Glu Thr Pro Val Pro Gly Ser Asp Leu Gln Val
    50                  55                  60

Cys Leu Pro Lys Gly Pro Thr Cys Cys Ser Arg Lys Met Glu Glu Lys
65                  70                  75                  80

Tyr Gln Leu Thr Ala Arg Leu Asn Met Glu Gln Leu Leu Gln Ser Ala
                85                  90                  95

Ser Met Glu Leu Lys Phe Leu Ile Ile Gln Asn Ala Ala Val Phe Gln
            100                 105                 110

Glu Ala Phe Glu Ile Val Val Arg His Ala Lys Asn Tyr Thr Asn Ala
        115                 120                 125

Met Phe Lys Asn Asn Tyr Pro Ser Leu Thr Pro Gln Ala Phe Glu Phe
    130                 135                 140

Val Gly Glu Phe Phe Thr Asp Val Ser Leu Tyr Ile Leu Gly Ser Asp
145                 150                 155                 160

Ile Asn Val Asp Asp Met Val Asn Glu Leu Phe Asp Ser Leu Phe Pro
                165                 170                 175

Val Ile Tyr Thr Gln Leu Met Asn Pro Gly Leu Pro Asp Ser Ala Leu
            180                 185                 190

Asp Ile Asn Glu Cys Leu Arg Gly Ala Arg Arg Asp Leu Lys Val Phe
        195                 200                 205

Gly Asn Phe Pro Lys Leu Ile Met Thr Gln Val Ser Lys Ser Leu Gln
    210                 215                 220

Val Thr Arg Ile Phe Leu Gln Ala Leu Asn Leu Gly Ile Glu Val Ile
225                 230                 235                 240

Asn Thr Thr Asp His Leu Lys Phe Ser Lys Asp Cys Gly Arg Met Leu
                245                 250                 255

Thr Arg Met Trp Tyr Cys Ser Tyr Cys Gln Gly Leu Met Met Val Lys
            260                 265                 270

Pro Cys Gly Gly Tyr Cys Asn Val Val Met Gln Gly Cys Met Ala Gly
        275                 280                 285

Val Val Glu Ile Asp Lys Tyr Trp Arg Glu Tyr Ile Leu Ser Leu Glu
    290                 295                 300

Glu Leu Val Asn Gly Met Tyr Arg Ile Tyr Asp Met Glu Asn Val Leu
305                 310                 315                 320

-continued

```
Leu Gly Leu Phe Ser Thr Ile His Asp Ser Ile Gln Tyr Val Gln Lys
                325                 330                 335

Asn Ala Gly Lys Leu Thr Thr Thr Ile Gly Lys Leu Cys Ala His Ser
            340                 345                 350

Gln Gln Arg Gln Tyr Arg Ser Ala Tyr Tyr Pro Glu Asp Leu Phe Ile
            355                 360                 365

Asp Lys Lys Val Leu Lys Val Ala His Val Glu His Glu Glu Thr Leu
    370                 375                 380

Ser Ser Arg Arg Arg Glu Leu Ile Gln Lys Leu Lys Ser Phe Ile Ser
385                 390                 395                 400

Phe Tyr Ser Ala Leu Pro Gly Tyr Ile Cys Ser His Ser Pro Val Ala
                405                 410                 415

Glu Asn Asp Thr Leu Cys Trp Asn Gly Gln Glu Leu Val Glu Arg Tyr
            420                 425                 430

Ser Gln Lys Ala Ala Arg Asn Gly Met Lys Asn Gln Phe Asn Leu His
            435                 440                 445

Glu Leu Lys Met Lys Gly Pro Glu Pro Val Val Ser Gln Ile Ile Asp
    450                 455                 460

Lys Leu Lys His Ile Asn Gln Leu Leu Arg Thr Met Ser Met Pro Lys
465                 470                 475                 480

Gly Arg Val Leu Asp Lys Asn Leu Asp Glu Glu Gly Phe Glu Ser Gly
                485                 490                 495

Asp Cys Gly Asp Asp Glu Asp Glu Cys Ile Gly Gly Ser Gly Asp Gly
            500                 505                 510

Met Ile Lys Val Lys Asn Gln Leu Arg Phe Leu Ala Glu Leu Ala Tyr
            515                 520                 525

Asp Leu Asp Val Asp Asp Ala Pro Gly Asn Ser Gln Gln Ala Thr Pro
    530                 535                 540

Lys Asp Asn Glu Ile Ser Thr Phe His Asn Leu Gly Asn Val His Ser
545                 550                 555                 560

Pro Leu Lys Leu Leu Thr Ser Met Ala Ile Ser Val Val Cys Phe Phe
                565                 570                 575

Phe Leu Val His
            580
```